(12) United States Patent
Huynh et al.

(10) Patent No.: US 9,588,110 B2
(45) Date of Patent: Mar. 7, 2017

(54) MULTI COMPONENT ANTIBODY BASED DETECTION TECHNOLOGY

(75) Inventors: Khanh Duc Huynh, Malden, MA (US); Wan Cheung Cheung, Lexington, MA (US); Roberto Polakiewicz, Lexington, MA (US)

(73) Assignee: CELL SIGNALING TECHNOLOGY, INC., Danvers, MA (US)

(*) Notice: Subject to any disclaimer, the term of this patent is extended or adjusted under 35 U.S.C. 154(b) by 77 days.

(21) Appl. No.: 14/235,555

(22) PCT Filed: Jul. 27, 2012

(86) PCT No.: PCT/US2012/048587
§ 371 (c)(1),
(2), (4) Date: Oct. 14, 2014

(87) PCT Pub. No.: WO2013/016653
PCT Pub. Date: Jan. 31, 2013

(65) Prior Publication Data
US 2015/0031563 A1    Jan. 29, 2015

Related U.S. Application Data

(60) Provisional application No. 61/512,682, filed on Jul. 28, 2011, provisional application No. 61/563,153, filed on Nov. 23, 2011.

(51) Int. Cl.
| | | |
|---|---|---|
| G01N 33/53 | (2006.01) | |
| C12N 9/52 | (2006.01) | |
| G01N 33/50 | (2006.01) | |
| C12Q 1/37 | (2006.01) | |
| G01N 33/542 | (2006.01) | |
| G01N 33/569 | (2006.01) | |
| G01N 33/574 | (2006.01) | |
| C07K 16/18 | (2006.01) | |

(52) U.S. Cl.
CPC ......... *G01N 33/5306* (2013.01); *C07K 16/18* (2013.01); *C12N 9/52* (2013.01); *C12Q 1/37* (2013.01); *G01N 33/50* (2013.01); *G01N 33/542* (2013.01); *G01N 33/56966* (2013.01); *G01N 33/57492* (2013.01); *C07K 2319/43* (2013.01); *C07K 2319/61* (2013.01); *C12Y 304/2207* (2013.01); *G01N 2800/60* (2013.01)

(58) Field of Classification Search
None
See application file for complete search history.

(56) References Cited

U.S. PATENT DOCUMENTS

| | | | |
|---|---|---|---|
| 4,208,479 A | * 6/1980 | Zuk | C07J 41/0016 435/7.72 |
| 6,773,706 B2 | 8/2004 | Schneewind et al. | |
| 7,101,692 B2 | 9/2006 | Schneewind et al. | |
| 7,776,553 B2 | 8/2010 | Love et al. | |
| 8,148,321 B2 | 4/2012 | Roy et al. | |
| 2006/0073530 A1 | 4/2006 | Schneewind et al. | |
| 2007/0298435 A1 | * 12/2007 | Aoyagi | G01N 33/542 435/7.1 |
| 2009/0088372 A1 | 4/2009 | Roy et al. | |
| 2011/0189664 A1 | 8/2011 | Dixon et al. | |

FOREIGN PATENT DOCUMENTS

| | | | |
|---|---|---|---|
| JP | EP 620438 | * | 6/1990 |
| WO | WO 2007/035633 A2 | | 3/2007 |
| WO | WO 2009/124086 A2 | | 10/2009 |
| WO | WO 2010/087994 A2 | | 8/2010 |
| WO | WO 2011/056911 A9 | | 5/2011 |
| WO | WO 2011/133704 A2 | | 10/2011 |

OTHER PUBLICATIONS

Popp et al. (Nature Chemical Biology 2007 vol. 3, p. 707-708).*
Pathasarathy et al. (Bioconjugate Chem. 2007 vol. 18, p. 469-476).*
Levary et al. (PlusOne 2011 vol. 6, e18342, total 6 pages).*
Sakamoto et al. (Bioconjugate Chem 2010 vol. 21, p. 2227-2233).*
Hendrickx, A.P.A. et al., "Architects at the bacterial surface—sortases and the assembly of pili with isopeptide bonds", Nature Reviews | Microbiology, (Mar. 2011), vol. 9, pp. 166-176.
Antos, J. M. et al., "A Straight Path to Circular Proteins", Journal of Biological History, (Jun. 5, 2009), vol. 284, No. 23, pp. 16028-16036.
Mortaji, L. E. et al., "Stability and Assembly of Pilus Subunits of *Streptococcus pneumoniae*", Journal of Biological Chemistry, (Apr. 16, 2010), vol. 285, No. 16, pp. 12405-12415.
Marraffini, L. A., et al., "Sortases and the Art of Anchoring Proteins to the Envelopes of Gram-Positive Bacteria", Microbiology and Molecular Biology Reviews, (Mar. 2006), vol. 70, No. 1, pp. 192-221.
Schneewind, O. et al., "Protein secretion and surface display in Gram-positive bacteria", Phil. Trans. R. Soc. B, (2012), vol. 367, pp. 1123-1139.
Spirig, T. et al., "Sortase enzymes in Gram-positive bacteria", Molecular Microbiology, (2011), vol. 82, No. 5, pp. 1044-1059.
International Search Report dated Oct. 23, 2012 issued in PCT/US2012/48587.

* cited by examiner

*Primary Examiner* — Jacob Cheu
(74) *Attorney, Agent, or Firm* — Scully Scott Murphy & Presser

(57) ABSTRACT

The disclosure provides methods for detecting the concurrent presence of at least two targets within a biological sample. The method includes contacting said biological sample with a first binding agent, said first binding agent operably linked to a first sortase molecule, wherein said first binding agent specifically binds to a first target; contacting said biological sample with a second binding agent, said second binding agent operably linked to a first sortase recognition sequence peptide, wherein said second binding agent specifically binds to a second target; adding a sortase substrate under conditions where a first sortase-mediated ligation of the sortase substrate to the first sortase recognition sequence will produce a ligation product, and detecting the ligation product, wherein detection of said ligation product indicates the concurrent presence of the first target and the second target in the biological sample. Also disclosed are kits comprising reagents for performing the methods as claimed.

21 Claims, 13 Drawing Sheets

| Erk1/2 | Erk1/2 | Erk1/2-Sdel59 | Erk1/2-Sdel59 | Akt1 | Akt1 | Akt1-Sdel59 | Akt1-Sdel59 | Stat3 | Stat3 |
|---|---|---|---|---|---|---|---|---|---|
| 0.063 | 0.053 | 0.077 | 0.067 | 0.114 | 0.119 | 0.148 | 0.169 | 0.061 | 0.060 |
| 0.063 | 0.051 | 0.098 | 0.068 | 0.203 | 0.216 | 0.209 | 0.192 | 0.054 | 0.050 |
| 0.061 | 0.050 | 0.084 | 0.076 | 0.587 | 0.625 | 0.451 | 0.391 | 0.053 | 0.050 |

B

| Erk1/2 | Erk1/2 | Erk1/2-Sdel59 | Erk1/2-Sdel59 | Akt1 | Akt1 | Akt1-Sdel59 | Akt1-Sdel59 | Stat3 | Stat3 |
|---|---|---|---|---|---|---|---|---|---|
| 2.161 | 2.127 | 1.746 | 1.629 | 0.066 | 0.063 | 0.094 | 0.091 | 0.062 | 0.062 |
| 2.720 | 2.687 | 2.460 | 2.417 | 0.058 | 0.061 | 0.089 | 0.085 | 0.056 | 0.055 |
| 3.103 | 3.070 | 2.929 | 2.743 | 0.057 | 0.057 | 0.102 | 0.479 | 0.053 | 0.053 |

C

| Erk1/2 | Erk1/2 | Erk1/2-Sdel59 | Erk1/2-Sdel59 | Akt1 | Akt1 | Akt1-Sdel59 | Akt1-Sdel59 | Stat3 | Stat3 |
|---|---|---|---|---|---|---|---|---|---|
| 0.064 | 0.062 | 0.084 | 0.074 | 0.060 | 0.058 | 0.075 | 0.087 | 1.282 | 1.108 |
| 0.059 | 0.056 | 0.092 | 0.087 | 0.055 | 0.054 | 0.085 | 0.101 | 1.367 | 1.541 |
| 0.061 | 0.052 | 0.090 | 0.098 | 0.053 | 0.055 | 0.084 | 0.095 | 1.951 | 1.782 |

| | Akt1 | Akt1 | Akt1-Sdel25 | Akt1-Sdel25 | Akt1-Sdel59 | Akt1-Sdel59 |
|---|---|---|---|---|---|---|
| Minus $G_{5x}$-biotin | 0.101 | 0.121 | 0.080 | 0.086 | 0.077 | 0.074 |
| | 0.088 | 0.090 | 0.074 | 0.083 | 0.079 | 0.067 |
| Plus $G_{5x}$-biotin | 0.314 | 0.252 | 0.782 | 0.736 | 0.815 | 0.582 |
| | 0.289 | 0.309 | 0.831 | 0.867 | 0.939 | 0.834 |

B

| | Akt1 | Akt1 | Akt1-Sdel25 | Akt1-Sdel25 | Akt1-Sdel59 | Akt1-Sdel59 |
|---|---|---|---|---|---|---|
| Minus $G_{5x}$-biotin | 0.069 | 0.073 | 0.070 | 0.063 | 0.058 | 0.056 |
| | 0.069 | 0.064 | 0.067 | 0.064 | 0.057 | 0.056 |
| Plus $G_{5x}$-biotin | 0.203 | 0.170 | 0.170 | 0.167 | 0.149 | 0.125 |
| | 0.215 | 0.205 | 0.191 | 0.180 | 0.174 | 0.168 |

| | Met | Met | Met | Met-Sdel59 | Met-Sdel59 | Met-Sdel59 |
|---|---|---|---|---|---|---|
| Minus G$_{5x}$-biotin | 0.074 | 0.078 | 0.064 | 0.062 | 0.061 | 0.069 |
| | 0.081 | 0.070 | 0.054 | 0.060 | 0.056 | 0.046 |
| Plus G$_{5x}$-biotin | 0.086 | 0.086 | 0.074 | 1.276 | 1.452 | 1.623 |
| | 0.104 | 0.096 | 0.091 | 1.372 | 1.436 | 1.491 |

B

| | Met | Met | Met | Met-Sdel59 | Met-Sdel59 | Met-Sdel59 |
|---|---|---|---|---|---|---|
| Minus G$_{5x}$-biotin | 0.128 | 0.107 | 0.079 | 0.071 | 0.064 | 0.070 |
| | 0.107 | 0.077 | 0.062 | 0.071 | 0.065 | 0.067 |
| Plus G$_{5x}$-biotin | 0.153 | 0.120 | 0.087 | 0.101 | 0.117 | 0.107 |
| | 0.110 | 0.115 | 0.086 | 0.108 | 0.108 | 0.110 |

C

| | Met | Met | Met | Met-Sdel59 | Met-Sdel59 | Met-Sdel59 |
|---|---|---|---|---|---|---|
| Minus G$_{5x}$-biotin | 0.166 | 0.094 | 0.069 | 0.066 | 0.061 | 0.068 |
| | 0.251 | 0.129 | 0.063 | 0.070 | 0.063 | 0.067 |
| Plus G$_{5x}$-biotin | 0.264 | 0.201 | 0.104 | 0.207 | 0.186 | 0.191 |
| | 0.228 | 0.205 | 0.099 | 0.180 | 0.236 | 0.199 |

SEQUENCE LISTING

```
<160> NUMBER OF SEQ ID NOS: 23

<210> SEQ ID NO 1
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 1

Leu Pro Xaa Thr Gly
1               5

<210> SEQ ID NO 2
<211> LENGTH: 5
<212> TYPE: PRT
<213> ORGANISM: Artificial Sequence
<220> FEATURE:
<223> OTHER INFORMATION: Synthetic Peptide
```

```
<400> SEQUENCE: 2

Asn Pro Gln Thr Asn
1               5

<210> SEQ ID NO 3
<211> LENGTH: 4
<212> TYPE: PRT
<213> ORGANISM: Artificial Sequence
<220> FEATURE:
<223> OTHER INFORMATION: Synthetic Peptide

<400> SEQUENCE: 3

Gly Gly Gly Gly
1

<210> SEQ ID NO 4
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 4

Gly Gly Gly Gly Gly
1               5

<210> SEQ ID NO 5
<211> LENGTH: 6
<212> TYPE: PRT
<213> ORGANISM: Artificial Sequence
<220> FEATURE:
<223> OTHER INFORMATION: Synthetic Peptide

<400> SEQUENCE: 5

Gly Gly Gly Gly Gly Gly
1               5

<210> SEQ ID NO 6
<211> LENGTH: 5
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa can be Ile or Leu
<220> FEATURE:
<221> NAME/KEY: MISC_FEATURE
<222> LOCATION: (2)..(2)
<223> OTHER INFORMATION: Xaa can be Pro or Ala
<220> FEATURE:
<221> NAME/KEY: misc_feature
<222> LOCATION: (3)..(3)
<223> OTHER INFORMATION: Xaa can be any naturally occurring amino acid

<400> SEQUENCE: 6

Xaa Xaa Xaa Thr Gly
1               5

<210> SEQ ID NO 7
<211> LENGTH: 5
<212> TYPE: PRT
<213> ORGANISM: Artificial Sequence
<220> FEATURE:
<223> OTHER INFORMATION: Synthetic Peptide
```

```
<400> SEQUENCE: 7

Leu Pro Asn Thr Ala
1               5

<210> SEQ ID NO 8
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa can be any naturally occurring amino acid

<400> SEQUENCE: 8

Leu Pro Xaa Thr Gly Gly Gly
1               5

<210> SEQ ID NO 9
<211> LENGTH: 7
<212> TYPE: PRT
<213> ORGANISM: Artificial Sequence
<220> FEATURE:
<223> OTHER INFORMATION: Synthetic Peptide

<400> SEQUENCE: 9

Asn Pro Gln Thr Gly Gly Gly
1               5

<210> SEQ ID NO 10
<211> LENGTH: 7
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (1)..(1)
<223> OTHER INFORMATION: Xaa can be Ile or Leu
<220> FEATURE:
<221> NAME/KEY: MISC_FEATURE
<222> LOCATION: (2)..(2)
<223> OTHER INFORMATION: Xaa can be Pro or Ala
<220> FEATURE:
<221> NAME/KEY: misc_feature
<222> LOCATION: (3)..(3)
<223> OTHER INFORMATION: Xaa can be any naturally occurring amino acid

<400> SEQUENCE: 10

Xaa Xaa Xaa Thr Gly Gly Gly
1               5

<210> SEQ ID NO 11
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 11

Asn Pro Lys Thr Asn
1               5

<210> SEQ ID NO 12
<211> LENGTH: 7
<212> TYPE: PRT
<213> ORGANISM: Artificial Sequence
```

```
<220> FEATURE:
<223> OTHER INFORMATION: Synthetic Peptide

<400> SEQUENCE: 12

Leu Pro Asn Thr Gly Gly Gly
1               5

<210> SEQ ID NO 13
<211> LENGTH: 9
<212> TYPE: PRT
<213> ORGANISM: Artificial Sequence
<220> FEATURE:
<223> OTHER INFORMATION: Synthetic Peptide
<220> FEATURE:
<221> NAME/KEY: misc_feature
<222> LOCATION: (3)..(3)
<223> OTHER INFORMATION: Xaa can be any naturally occurring amino acid

<400> SEQUENCE: 13

Leu Pro Xaa Thr Gly Gly Gly Gly Gly
1               5

<210> SEQ ID NO 14
<211> LENGTH: 9
<212> TYPE: PRT
<213> ORGANISM: Artificial Sequence
<220> FEATURE:
<223> OTHER INFORMATION: Synthetic Peptide

<400> SEQUENCE: 14

Asn Pro Gln Thr Gly Gly Gly Gly Gly
1               5

<210> SEQ ID NO 15
<211> LENGTH: 5
<212> TYPE: PRT
<213> ORGANISM: Artificial Sequence
<220> FEATURE:
<223> OTHER INFORMATION: Synthetic Peptide

<400> SEQUENCE: 15

Leu Pro Asn Thr Gly
1               5

<210> SEQ ID NO 16
<211> LENGTH: 206
<212> TYPE: PRT
<213> ORGANISM: Staphylococcus aureus

<400> SEQUENCE: 16

Met Lys Lys Trp Thr Asn Arg Leu Met Thr Ile Ala Gly Val Val Leu
1               5                   10                  15

Ile Leu Val Ala Ala Tyr Leu Phe Ala Lys Pro His Ile Asp Asn Tyr
            20                  25                  30

Leu His Asp Lys Asp Lys Asp Glu Lys Ile Glu Gln Tyr Asp Lys Asn
        35                  40                  45

Val Lys Glu Gln Ala Ser Lys Asp Asn Lys Gln Gln Ala Lys Pro Gln
    50                  55                  60

Ile Pro Lys Asp Lys Ser Lys Val Ala Gly Tyr Ile Glu Ile Pro Asp
65                  70                  75                  80

Ala Asp Ile Lys Glu Pro Val Tyr Pro Gly Pro Ala Thr Pro Glu Gln
                85                  90                  95

Leu Asn Arg Gly Val Ser Phe Ala Glu Glu Asn Glu Ser Leu Asp Asp
                100                 105                 110
```

Gln Asn Ile Ser Ile Ala Gly His Thr Phe Ile Asp Arg Pro Asn Tyr
            115                 120                 125

Gln Phe Thr Asn Leu Lys Ala Ala Lys Lys Gly Ser Met Val Tyr Phe
        130                 135                 140

Lys Val Gly Asn Glu Thr Arg Lys Tyr Lys Met Thr Ser Ile Arg Asp
145                 150                 155                 160

Val Lys Pro Thr Asp Val Glu Val Leu Asp Glu Gln Lys Gly Lys Asp
                165                 170                 175

Lys Gln Leu Thr Leu Ile Thr Cys Asp Asp Tyr Asn Glu Lys Thr Gly
                180                 185                 190

Val Trp Glu Lys Arg Lys Ile Phe Val Ala Thr Glu Val Lys
            195                 200                 205

<210> SEQ ID NO 17
<211> LENGTH: 246
<212> TYPE: PRT
<213> ORGANISM: Streptococcus pyogenes

<400> SEQUENCE: 17

Met Ile Ser Gln Arg Met Met Met Thr Ile Val Gln Val Ile Asn Lys
1               5                   10                  15

Ala Ile Asp Thr Leu Ile Leu Ile Phe Cys Leu Val Val Leu Phe Leu
            20                  25                  30

Ala Gly Phe Gly Leu Trp Asp Ser Tyr His Leu Tyr Gln Gln Ala Asp
        35                  40                  45

Ala Ser Asn Phe Lys Lys Phe Lys Thr Ala Gln Gln Gln Pro Lys Phe
    50                  55                  60

Glu Asp Leu Leu Ala Leu Asn Glu Asp Val Ile Gly Trp Leu Asn Ile
65                  70                  75                  80

Pro Gly Thr His Ile Asp Tyr Pro Leu Val Gln Gly Lys Thr Asn Leu
                85                  90                  95

Glu Tyr Ile Asn Lys Ala Val Asp Gly Ser Val Ala Met Ser Gly Ser
            100                 105                 110

Leu Phe Leu Asp Thr Arg Asn His Asn Asp Phe Thr Asp Asp Tyr Ser
        115                 120                 125

Leu Ile Tyr Gly His His Met Ala Gly Asn Ala Met Phe Gly Glu Ile
    130                 135                 140

Pro Lys Phe Leu Lys Lys Asp Phe Phe Asn Lys His Asn Lys Ala Ile
145                 150                 155                 160

Ile Glu Thr Lys Glu Arg Lys Lys Leu Thr Val Thr Ile Phe Ala Cys
                165                 170                 175

Leu Lys Thr Asp Ala Phe Asp Gln Leu Val Phe Asn Pro Asn Ala Ile
                180                 185                 190

Thr Asn Gln Asp Gln Gln Arg Gln Leu Val Asp Tyr Ile Ser Lys Arg
            195                 200                 205

Ser Lys Gln Phe Lys Pro Val Lys Leu Lys His His Thr Lys Phe Val
        210                 215                 220

Ala Phe Ser Thr Cys Glu Asn Phe Ser Thr Asp Asn Arg Val Ile Val
225                 230                 235                 240

Val Gly Thr Ile Gln Glu
                245

<210> SEQ ID NO 18
<211> LENGTH: 266
<212> TYPE: PRT
<213> ORGANISM: Bacillus cereus -continued

<400> SEQUENCE: 18

Met Lys Arg Asn Leu Val Leu Gly Gly Ile Phe Leu Phe Gly Leu Gly
1               5                   10                  15

Ile Phe Leu Tyr Pro Thr Ile Ser Asn Trp Leu Ala Thr Arg Ala His
            20                  25                  30

Tyr Ser Glu Ile Ser Ser Tyr Asp Lys Lys Ile Lys Ala Leu Gln Lys
        35                  40                  45

Lys Glu Val Glu Arg Arg Glu Lys Glu Ala Ala Glu Tyr Asn Lys Gln
    50                  55                  60

Val Gln Thr Ser Thr Lys Thr Phe Thr Asp Pro Phe Ser Glu Lys Lys
65                  70                  75                  80

Ser Asn His Gln Ala Tyr Ala Asp Ala Leu Asn Leu Gly Asp Val Met
                85                  90                  95

Gly Tyr Ile Glu Ile Ser Lys Ile Asn Ile Lys Leu Pro Ile Tyr Gln
            100                 105                 110

Gly Thr Ser Glu Glu Val Leu Ser Arg Gly Ile Gly His Leu Asp Phe
        115                 120                 125

Ser Ser Leu Pro Val Gly Gly Glu Asn Thr His Thr Ile Leu Thr Gly
    130                 135                 140

His Arg Gly Leu Pro Ser Ala Lys Leu Phe Thr Asp Leu Asp Lys Leu
145                 150                 155                 160

Ser Lys Gly Asp Leu Phe Tyr Leu His Ser Leu Asp Lys Val Leu Ala
                165                 170                 175

Tyr Lys Val Asp Gln Ile Lys Val Val Leu Pro His Glu Thr Asp Asp
            180                 185                 190

Leu Gln Ile Val Gln Asn Lys Asp Tyr Thr Thr Leu Ile Thr Cys Thr
        195                 200                 205

Pro Tyr Gly Ile Asn Thr Asn Arg Leu Leu Val Arg Gly Glu Arg Val
    210                 215                 220

Glu Leu Asn Glu Lys Glu Lys Gln Lys Val Ser Thr Glu Ile Val Ile
225                 230                 235                 240

Phe Asn Lys Trp Thr Val Ile Val Thr Ile Leu Leu Leu Cys Val Phe
                245                 250                 255

Leu Val Glu Ile Tyr Lys Lys Arg Phe Thr
            260                 265

<210> SEQ ID NO 19
<211> LENGTH: 211
<212> TYPE: PRT
<213> ORGANISM: Bacillus cereus

<400> SEQUENCE: 19

Met Glu Lys Gly Lys Lys Val His Lys Arg Lys Ser Lys Trp Ile Leu
1               5                   10                  15

Val Ile Ile Gly Ile Leu Val Ser Ile Ile Leu Phe Gly Phe Gly Ile
            20                  25                  30

Val Ala Phe Phe Gly Trp Glu Leu Thr Lys Gln Thr Ala Leu Leu Ala
        35                  40                  45

His Thr Val Ile Thr Pro Tyr Lys Pro Val Glu Gln Glu Lys Glu Phe
    50                  55                  60

Asn Gln Val Trp Ser Lys Ile Pro Asp Pro Gly Glu Lys Leu Gly Glu
65                  70                  75                  80

Leu Lys Phe Pro Ser Leu Ser Tyr Glu Val Pro Val Val Glu Gly Thr
                85                  90                  95

```
His Pro Lys Glu Leu Glu Ser Gly Val Gly His Phe Ala Gly Ser Thr
            100                 105                 110

Leu Pro Gly Gln Gly Gly Asn Val Val Leu Ser Gly His Arg Asn Thr
        115                 120                 125

Ser Phe Arg Lys Leu Glu Asp Val Lys Lys Gly Asp Gln Ile Lys Phe
    130                 135                 140

Ala Thr Pro Tyr Gly Glu Phe Val Tyr Glu Ile Thr Asp Phe Lys Ile
145                 150                 155                 160

Thr Gly Ala Lys Asp Glu Asn Ile Ile Val Pro Thr Asp Tyr Glu Thr
                165                 170                 175

Leu Thr Leu Thr Thr Cys Tyr Pro Phe Glu Tyr Ile Gly Asp Ala Pro
            180                 185                 190

Asp Arg Phe Ile Val Tyr Thr Lys Ile Val Ser Lys Pro Asp Leu Lys
        195                 200                 205

Lys Gln Ser
        210

<210> SEQ ID NO 20
<211> LENGTH: 181
<212> TYPE: PRT
<213> ORGANISM: Staphylococcus aureus

<400> SEQUENCE: 20

Lys Pro His Ile Asp Asn Tyr Leu His Asp Lys Asp Lys Asp Glu Lys
1               5                   10                  15

Ile Glu Gln Tyr Asp Lys Asn Val Lys Glu Gln Ala Ser Lys Asp Asn
            20                  25                  30

Lys Gln Gln Ala Lys Pro Gln Ile Pro Lys Asp Lys Ser Lys Val Ala
        35                  40                  45

Gly Tyr Ile Glu Ile Pro Asp Ala Asp Ile Lys Glu Pro Val Tyr Pro
    50                  55                  60

Gly Pro Ala Thr Pro Glu Gln Leu Asn Arg Gly Val Ser Phe Ala Glu
65                  70                  75                  80

Glu Asn Glu Ser Leu Asp Asp Gln Asn Ile Ser Ile Ala Gly His Thr
                85                  90                  95

Phe Ile Asp Arg Pro Asn Tyr Gln Phe Thr Asn Leu Lys Ala Ala Lys
            100                 105                 110

Lys Gly Ser Met Val Tyr Phe Lys Val Gly Asn Glu Thr Arg Lys Tyr
        115                 120                 125

Lys Met Thr Ser Ile Arg Asp Val Lys Pro Thr Asp Val Glu Val Leu
    130                 135                 140

Asp Glu Gln Lys Gly Lys Asp Lys Gln Leu Thr Leu Ile Thr Cys Asp
145                 150                 155                 160

Asp Tyr Asn Glu Lys Thr Gly Val Trp Glu Lys Arg Lys Ile Phe Val
                165                 170                 175

Ala Thr Glu Val Lys
            180

<210> SEQ ID NO 21
<211> LENGTH: 147
<212> TYPE: PRT
<213> ORGANISM: Staphylococcus aureus
```

<400> SEQUENCE: 21

```
Gln Ala Lys Pro Gln Ile Pro Lys Asp Lys Ser Lys Val Ala Gly Tyr
1               5                   10                  15

Ile Glu Ile Pro Asp Ala Asp Ile Lys Glu Pro Val Tyr Pro Gly Pro
            20                  25                  30

Ala Thr Pro Glu Gln Leu Asn Arg Gly Val Ser Phe Ala Glu Glu Asn
        35                  40                  45

Glu Ser Leu Asp Asp Gln Asn Ile Ser Ile Ala Gly His Thr Phe Ile
    50                  55                  60

Asp Arg Pro Asn Tyr Gln Phe Thr Asn Leu Lys Ala Lys Lys Gly
65                  70                  75                  80

Ser Met Val Tyr Phe Lys Val Gly Asn Glu Thr Arg Lys Tyr Lys Met
                85                  90                  95

Thr Ser Ile Arg Asp Val Lys Pro Thr Asp Val Glu Val Leu Asp Glu
            100                 105                 110

Gln Lys Gly Lys Asp Lys Gln Leu Thr Leu Ile Thr Cys Asp Asp Tyr
        115                 120                 125

Asn Glu Lys Thr Gly Val Trp Glu Lys Arg Lys Ile Phe Val Ala Thr
    130                 135                 140

Glu Val Lys
145

<210> SEQ ID NO 22
<211> LENGTH: 8
<212> TYPE: PRT
<213> ORGANISM: Artificial Sequence
<220> FEATURE:
<223> OTHER INFORMATION: Synthetic Peptide

<400> SEQUENCE: 22

Asp Tyr Lys Asp Asp Asp Asp Lys
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic Peptide
<220> FEATURE:
<221> NAME/KEY: MISC_FEATURE
<222> LOCATION: (3)..(3)
<223> OTHER INFORMATION: Xaa can be Gln or Lys
<220> FEATURE:
<221> NAME/KEY: MISC_FEATURE
<222> LOCATION: (4)..(4)
<223> OTHER INFORMATION: Xaa can be Thr or Ser
<220> FEATURE:
<221> NAME/KEY: MISC_FEATURE
<222> LOCATION: (5)..(5)
<223> OTHER INFORMATION: Xaa can be Asn, Gly, or Ser
<220> FEATURE:
<221> NAME/KEY: MISC_FEATURE
<222> LOCATION: (6)..(6)
<223> OTHER INFORMATION: Xaa can be Asp or Ala

<400> SEQUENCE: 23

Asn Pro Xaa Xaa Xaa Xaa
1               5
```

MULTI COMPONENT ANTIBODY BASED DETECTION TECHNOLOGY

CROSS-REFERENCE TO RELATED APPLICATIONS

This application claims priority to U.S. provisional application Ser. No. 61/512,682, filed on Jul. 28, 2011, and U.S. provisional application Ser. No. 61/563,153, filed on Nov. 23, 2011. The contents of the foregoing applications are incorporated by reference in the present disclosure.

BACKGROUND

Many disease conditions (such as cancer and heart disease) are characterized by the co-expression of two or more disease marker in a diseased cell or a cell developing the disease. Such changes may be difficult to elucidate. For example, Dewey et al., Circ Cardiovasc Genet. 4:26-35, 2011 describes fifty fetal gene coexpression modules in developing myocardium that were not present in normal adult tissue. Of these fifty, three (6%) were reproduced in hypertrophied myocardium and seven (14%) were reproduced in failing myocardium. One fetal module was common to both failing and hypertrophied myocardium.

Similarly, many cancers show co-expression of disease markers. For example, breast cancer cells co-express several hormonal markers (see, e.g., Yang et al., Cancer Res. 67:10608-17, 2007). Likewise, Hodgkin's disease cells co-express CD20 and CD15 (see Zukerberg et al., Am. J. Pathol. 139: 475-483, 1991).

Methods to detect co-expression of two different markers have been described, For example, fluorescence (or Förster) resonance energy transfer (FRET) is a distance-dependent physical process by which energy is transferred nonradiatively from an excited molecular fluorophore (the donor) to another fluorophore (the acceptor). The use of FRET has been widely described in biology (see, e.g., Didenko, V. V., Biotechniques 31: 1106-21, 2001; Sekar and Periamsary, J. Cell Biol. 160: 629-633, 2003; Buntru et al., BMC Biology 2009, 7:81-91, 2009; and Ciruela, F. *Curr Opin Biotechnol.* 19:338-343, 2008). In fluorescence microscopy, as well as in molecular biology, FRET is a useful tool to quantify co-expression of two markers, as well as molecular dynamics between the two markers, such as protein-protein interactions, protein-DNA interactions, and protein conformational changes. For monitoring the complex formation between two molecules, one of them is labeled with a donor and the other with an acceptor, and these fluorophore-labeled molecules are mixed. When they are dissociated, the donor emission is detected upon the donor excitation. On the other hand, when the donor and acceptor are in proximity (1-10 nm) due to the interaction of the two molecules, the acceptor emission is predominantly observed because of the intermolecular FRET from the donor to the acceptor. For monitoring protein conformational changes, the target protein is labeled with a donor and an acceptor at two loci. When a twist or bend of the protein brings the change in the distance or relative orientation of the donor and acceptor, FRET change is observed. If a molecular interaction or a protein conformational change is dependent on ligand binding, this FRET technique is applicable to fluorescent indicators for the ligand detection. Two typical FRET pairs are cyan fluorescent protein and yellow fluorescent protein. These green fluorescent protein variants are easily attached to host proteins. Resonance energy transfer using bioluminescent molecules (e.g., luciferase) instead of cyan fluorescent protein is called BRET and has also been described.

Additional known methods for specific targeting two or more molecular targets in a biological sample that uses a combinatorial target approach are the bimolecular fluorescence complementation (BiFC) and the proximity ligation assay (PLA) (reviewed in Weibrecht, I., *Expert Rev Proteomics.* 7:401-409, 2010).

All of the known techniques for detecting more than one target simultaneously in a biological sample, however, are difficult to perform and require expensive reagents and the use of highly specific microscopes and other detection devices. Thus, it would be useful to have a less expensive, easier to perform method to detect co-expression of two or more markers in a biological sample.

SUMMARY

The present disclosure is based, at least in part, on the development of simple, easy-to-use methods for detecting the co-expression of two targets within a biological sample. Such methods can be useful, for example, to detect whether or not a cell or tissue is affected by a disease condition (e.g., cancer, heart disease, irritable bowel syndrome (IBD), Alzheimer's disease, or any other type disease with a genetic component (e.g., diabetes)).

The present disclosure relates to methods and compositions that can be utilized in various combinations for the highly specific identification, visualization and/or quantification of a plurality of targets in a sample, such as multiple protein and nucleic acid targets in a tissue sample. In particular, the present disclosure relates to a multi-component binding agent (e.g., antibody)-based detection technology, which can be utilized to detect the concurrent presence of more than one target within a biological sample. The present disclosure further relates to the use of such multi-component detection technology in multiplex assay screening, immunohistochemistry, immunofluorescence, flow cytometry, and protein arrays, and kits comprising the components for using the technology.

Accordingly, in a first aspect, the present disclosure provides a method for detecting the concurrent presence of at least two targets within a biological sample. The method includes (a) contacting said biological sample with a first binding agent, said first binding agent operably linked to a first sortase molecule, wherein said first binding agent specifically binds to a first target; (b) contacting said biological sample with a second binding agent, said second binding agent operably linked to a first sortase recognition sequence peptide, wherein said second binding agent specifically binds to a second target; (c) adding a sortase substrate under conditions where a first sortase-mediated ligation of the sortase substrate to the first sortase recognition sequence will produce a ligation product, and (d) detecting the ligation product, wherein detection of said ligation product indicates the concurrent presence of the first target and the second target in the biological sample.

In another aspect, the present disclosure provides a method for detecting the concurrent presence of at least three targets within a biological sample. The method includes (a) contacting said biological sample with a first binding agent, said first binding agent operably linked to a first sortase molecule, wherein said first binding agent specifically binds to a first target; (b) contacting said biological sample with a second binding agent, said second binding agent operably linked to a first sortase recognition sequence peptide, wherein said second binding agent specifically binds to a second target; (c) contacting said biological sample with a third binding agent, said third binding agent operably linked to a second sortase molecule; (d) adding an intermediate reagent comprising a sortase substrate conjugated to a second sortase recognition sequence peptide under conditions where a first sortase-mediated ligation of the intermediate reagent to the first sortase recognition sequence will produce an intermediate product, (e) adding a sortase substrate under conditions where a second sortase-mediated ligation of the sortase substrate to the second sortase recognition sequence peptide on the intermediate product will produce a ligation product, and (f) detecting the second ligation product, wherein detection of said ligation product indicates the concurrent presence of the first target, the second target, and the third target in the biological sample.

In various embodiments, the first target is on a first molecule, the second target is on a second molecule, and the third target is on a third molecule.

In some embodiments, the first target and the second target are on the same molecule. In some embodiments, the first target, second target, and third target are on the same molecule.

In various embodiments, the first binding agent, second binding agent, third binding agent, and/or fourth binding agent is an antibody (e.g., a polyclonal or monoclonal antibody).

In various embodiments, the biological sample from a cell, a biopsy sample, a blood sample, a tissue sample, a saliva sample, a tear sample, a semen sample, cerebrospinal fluid sample, a bone marrow sample, a bone marrow sample, or a circulating tumor cell sample. In various embodiments, the biological sample is from a human. In some embodiments, the human has or is suspected of having a disease condition (e.g., heart disease or cancer)

In various embodiments of the various aspects of the methods and compositions disclosed herein, the first sortase molecule is a Sortase A molecule (e.g., a Sortase A molecule from *Staphylococcus aureus* or *Streptococcus pyogenes*). In various embodiments, the first sortase recognition sequence peptide comprises the amino acid sequence LPXTG, where X is any amino acid residue (SEQ ID NO: 1). In various embodiments, the second sortase molecule is a Sortase B molecule. In various embodiments, the second sortase recognition sequence peptide comprises the amino acid sequence NPQTN (SEQ ID NO: 2).

In various embodiments, the sortase substrate comprises the amino acid sequence GGG, or GGGG (SEQ ID NO: 3), or GGGGG (SEQ ID NO: 4), or GGGGGG (SEQ ID NO: 5).

In various embodiments of the various aspects of the disclosure, detecting the ligation product performed using a fourth binding agent that specifically binds to the ligation product. In some embodiments, the fourth binding agent is detectable.

In various embodiments, the first sortase molecule is directly attached to the first binding agent. In various embodiments, the first sortase molecule is indirectly attached to the first binding agent. In various embodiments, the first sortase molecule is directly attached to a first member of a first binding member pair and the first binding agent is directly attached to a second member of the first binding member pair.

In various embodiments, the first sortase recognition sequence peptide is directly attached to the second binding agent. In various embodiments, the first sortase recognition sequence peptide is indirectly attached to the second binding agent. In various embodiments, the first sortase recognition sequence is directly attached to a first member of a second binding member pair and the second binding agent is directly attached to a second member of the second binding member pair.

In various embodiments, the second sortase molecule is directly attached to the third binding agent. In various embodiments, the second sortase molecule is indirectly attached to the third binding agent. In various embodiments, the second sortase molecule is directly attached to a first member of a third binding member pair and the third binding agent is directly attached to a second member of the third binding member pair.

In various embodiments of the various aspects of the disclosure, the sortase substrate is operably linked to a first member of a fourth binding member pair. In various embodiments, the ligation product is detected using a second member of the fourth binding member pair. In some embodiments, the second member of the fourth binding member pair is detectable.

In various embodiments of the various aspects of the disclosure, each of the first binding member pair, second binding member pair, third binding member pair, or fourth binding member pair is selected from the group consisting of an avidin/biotin pair, a streptavidin/biotin pair, an antibody/antigen pair, a GST/glutathione pair, and a HIS tag/nickel or cobalt ion-containing substance.

In various embodiments, where the binding member pair is an antibody/antigen pair, the antigen is an Fc portion of an antibody of a species (i.e., the species of the antibody that specifically to a target) and the antibody (e.g., the antibody to which is attached a sortase molecule or a sortase recognition sequence) specifically binds to the Fc portion of the antibody of the species. In some embodiments, the species may be a mouse, a rabbit, a human, a hamster, a goat, a horse, a rat, or a sheep.

In further embodiments, where the binding member pair is an antibody/antigen pair, the antigen may be an epitope tag (e.g., a HIS tag, a FLAG tag, a myc tag, an HA tag, an HSV tag, a V5 tag, or a VSV-G tag) on the antibody that specifically binds to a target) and the antibody (e.g., to which is attached a sortase molecule or a sortase recognition sequence) specifically binds to the epitope tag (e.g., a FLAG-tag is the antigen and the antibody is a FLAG-specific antibody).

In yet another aspect, the present disclosure provides kits for detecting multiple targets concurrently that include two or more of (in any combination): (i) a first sortase recognition sequence directly attached to a first member of a first binding member pair, (ii) a first sortase molecule directly attached to a first member of a second binding member pair; (iii) a sortase substrate; and (iv) instructions for using the kit to detect the concurrent presence of at least two targets within a biological sample.

In some embodiments, the sortase substrate is directly attached to a first member of a third binding member pair. In some embodiments, the kit further comprises a detectable second member of the third binding member pair.

In another aspect, the disclosure features compositions that include a binding agent (e.g., an antibody) operably linked (e.g., covalently or non-covalently linked) to a sortase molecule. In some embodiments, the sortase molecule is a sortase A, sortase B, sortase C, or sortase D molecule (e.g., a sortase molecule described herein).

In a further aspect, the disclosure features compositions that include a binding agent (e.g., an antibody) operably linked (e.g., covalently or non-covalently linked) to a sortase recognition sequence peptide. In some embodiments, the sortase recognition sequence peptide includes a sequence selected from LPXTG (SEQ ID NO: 1), NPQTN (SEQ ID NO: 2), NPKTN (SEQ ID NO: 11), NP(Q/K)(T/S)(N/G/S)(D/A) (SEQ ID NO: 23), (I/L)(P/A)XTG (SEQ ID NO: 6), and LPNTA (SEQ ID NO: 7).

In another aspect, the disclosure features compositions that include a binding agent (e.g., an antibody) operably linked (e.g., covalently or non-covalently linked) to a sortase ligation product. In some embodiments, the sortase ligation product includes a sequence selected from LPXTGGG (where X is any amino acid) (SEQ ID NO: 8), NPQTGGG (SEQ ID NO: 9), (I/L)(P/A)XTGGG (SEQ ID NO: 10), and LPNTGGG (SEQ ID NO: 12). In some embodiments, the composition includes a structure having the formula:

binding agent—sortase ligation product—detectable moiety wherein each — can include a covalent or noncovalent linkage and can incorporate additional molecules or moieties (e.g., binding pair members, linkers (peptide or chemical linkers).

In some embodiments, the first binding member pair and the second binding member pair is each an antibody/antigen pair, where the antigen is an Fc portion of an antibody of a species and the antibody specifically binds to the Fc portion of the antibody of the species, wherein the species of the first binding member pair and the species of the second binding member pair are not the same. In some embodiments, the species of the first binding member pair is a rabbit and the species of the second binding member pair is a mouse.

BRIEF DESCRIPTION OF THE DRAWINGS

As shown in FIG. 3, two primary antibodies of different species (each specifically binding to Target 1 or Target 2) are added to the biological sample. Following washing to remove unbound antibodies, secondary antibodies are added, where the first of the secondary antibodies specifically binds to one of the two species (e.g., a rabbit IgG) and is attached to Sortase A and the second secondary antibody specifically binds to the other species (e.g., a mouse IgG2a) and is attached to LPXTG (SEQ ID NO: 1). Following washing, the poly-glycine-attached to antigen (circle) is added. If both Target 1 and Target 2 are present in the sample, the Sortase A will ligate the poly-glycine-attached to antigen to the second secondary antibody. The presence of this second secondary antibody can then be detected with an antibody that specifically binds the antigen.

As shown in FIG. 4, two primary antibodies (each specifically binding to Target 1 or Target 2 and each attached to either GST or biotin) are added to the biological sample. Following washing to remove unbound antibodies, sortase reagents are added. In this example, the binding member pair reactions utilized are the GST-glutathione binding member pair and the streptavidin-biotin binding member pair. Thus, the sortase reagents are Sortase A and the sortase A recognition sequence (i.e., LPXTG; SEQ ID NO: 1) attached to either glutathione or streptavidin. After washing to remove unbound sortase reagents, a reagent comprising a polyG-His tag is added. If both targets are present, the polyG-His tag reagent will be ligated by sortase to the LPXTG-attached reagent (in this case, streptavidin). The presence of the sortase ligation product (i.e., streptavidin-LPXT-polyG-His tag) can then be detected using a Nickel or Cobalt ion-containing compound.

FIGS. 7A-7C are a series of tables showing that the AB-SrtA fusions retain antigen specificity. Peptide-specific ELISA analysis on plates coated with the cognate peptide for Akt1 (FIG. 7A), Erk1/2 (FIG. 7B) and Stat3 (FIG. 7C; negative control). For each antibody species serial dilutions were done (rows; increasing concentration going down), each in duplicates (column pair). Expected binding of the test antibodies to their respective peptides is highlighted in grey.

FIGS. 9A-9B are tables showing the raw ELISA data presented graphically in FIG. 8. Plates are coated with the cognate peptides for Akt1-rpS6 (FIG. 9A) or Akt1-Stat3 (FIG. 9B).

FIGS. 11A, 11B, and 11C are tables showing raw ELISA data, the G5x-biotin rows of which presented graphically in FIG. 10. Plates are coated with the peptides of pMET-MET (FIG. 11A), Akt1-MET (FIG. 11B), and pMET-Akt1 (FIG. 11C).

FIGS. 12A-12C show A431 cells treated with EGF. FIGS. 12D-12F show untreated A431 cells. The cells were stained as follows: FIGS. 12A and 12D were stained with Hoescht dye, which highlights the nuclei. FIGS. 12B and 12E show detection of the ligated G5x-HA peptide. Specific signal in treated cells in FIG. 12B (i.e., membrane localized) but not in untreated cells in FIG. 12E indicates binding of both the EGFR-LPXTG and pEGFR-SrtA antibodies in the former and not the latter. FIGS. 12C and 12F show membrane localized signals indicating presumptive binding of both the EGFR-LPXTG and pEGFR-SrtA in EGF treated cells (FIG. 12C) and binding of only the EGFR-LPXTG in untreated cells (FIG. 12F) that do not have EGFR phosphorylated.

FIGS. 13A-13C show A431 cells treated with EGF. FIGS. 13D-13F show untreated A431 cells. The cells were stained as follows: FIGS. 13A and 13D were stained with Hoescht dye, which highlights the nuclei. FIGS. 13B and 13E show detection of the ligated G5x-FLAG peptide. Specific signal in treated cells in FIG. 13B (i.e., membrane localized) but not in untreated cells in FIG. 13E indicates binding of both the EGFR-LPXTG and pEGFR-SrtA antibodies in the former and not the latter. FIGS. 13C and 13F show membrane localized signals indicating presumptive binding of both the EGFR-LPXTG and pEGFR-SrtA in EGF treated cells (FIG. 13C) and binding of only the EGFR-LPXTG in untreated cells (FIG. 13F) that do not have EGFR phosphorylated.

DETAILED DESCRIPTION

Figure 1:
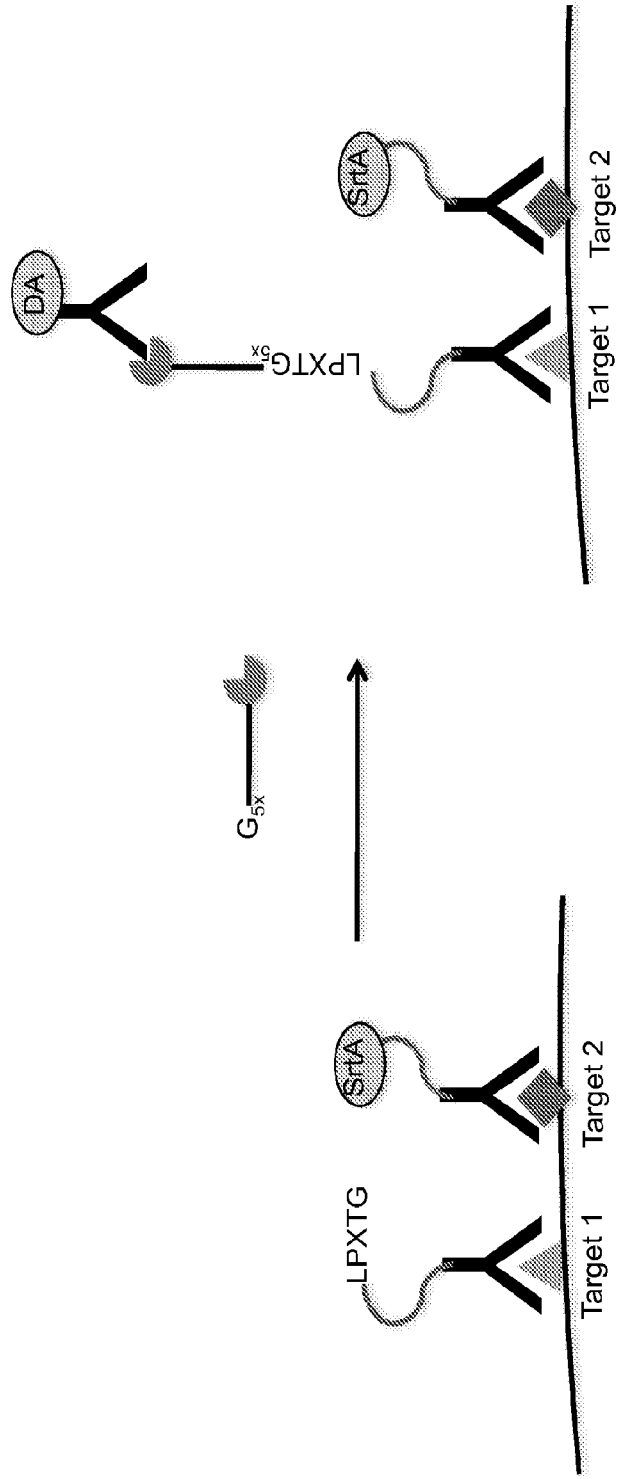
FIG. 1 is a schematic representation showing the mechanism of a non-limiting method of the present disclosure. As shown, SrtA-linked and LPXTG-linked antibodies, two non-limiting binding agents of the invention, are first allowed to bind to their respective targets, designated "Target 1" and "Target 2". Following removal of unbound antibodies a $(G)_{5x}$-ligand bearing an antigenic moiety (depicted as a ¾ circle) is added. As schematized here, only engagement of both targets will result in a ligated product, namely a LPXTG5x-ligand bearing antigenic moiety, that can be detected with a third antibody that specifically binds to the antigen moiety appropriate detection agent(s), designated "DA".

The present disclosure stems, at least in part, from the development of methods and compositions for detecting multiple targets in a biological sample.

The published patents, patent applications, websites, company names, and scientific literature referred to herein establish the knowledge that is available to those with skill in the art and are hereby incorporated by reference in their entirety to the same extent as if each was specifically and individually indicated to be incorporated by reference. Any conflict between any reference cited herein and the specific teachings of this specification shall be resolved in favor of the latter.

The further aspects, advantages, and embodiments of the new methods and compositions are described in more detail below. The patents, published applications, and scientific literature referred to herein establish the knowledge of those with skill in the art and are hereby incorporated by reference in their entirety to the same extent as if each was specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter. As used herein, the following terms have the meanings indicated. As used in this specification, the singular forms "a," "an" and "the" specifically also encompass the plural forms of the terms to which they refer, unless the content clearly dictates otherwise. The term "about" is used herein to mean approximately, in the region of, roughly, or around. When the term "about" is used in conjunction with a numerical range, it modifies that range by extending the boundaries above and below the numerical values set forth. In general, the term "about" is used herein to modify a numerical value above and below the stated value by a variance of 20%.

Technical and scientific terms used herein have the meaning commonly understood by one of skill in the art to which the present disclosure pertains, unless otherwise defined. Reference is made herein to various methodologies and materials known to those of skill in the art. Standard reference works setting forth the general principles of recombinant DNA technology, all of which are incorporated herein by reference in their entirety, include Ausubel et al. Current Protocols in Molecular Biology, John Wiley & Sons, New York, N.Y. (1989 and updates through August 2011), Sambrook et al., Molecular Cloning: A Laboratory Manual, 2nd Ed., Cold Spring Harbor Laboratory Press, New York (1989); Kaufman et al., Eds., Handbook of Molecular and Cellular Methods in Biology in Medicine, CRC Press, Boca Raton (1995); McPherson, Ed., Directed Mutagenesis: A Practical Approach, IRL Press, Oxford (1991). Standard reference works setting forth the general principles of pharmacology, all of which are incorporated herein by reference in their entirety, include Goodman and Gilman's The Pharmacological Basis of Therapeutics, 11th Ed., McGraw Hill Companies Inc., New York (2006); and Remington: The Science and Practice of Pharmacy, 21$^{st}$ Edition, Lippincott Williams & Wilkins, 2005.

In accordance with the various methods and compositions of the present disclosure, the biological activity of the bacterial enzyme, sortase, in being able to physically link two molecules is harnessed and used to facilitate detection of co-expression of two different targets in a biological sample. By utilizing the properties of sortases (e.g., Sortase A), the inventors developed a simple technique for detecting the co-expression of two molecules in a biological sample. This technique can be effected simply and at low cost to the user.

Accordingly, in a first aspect, the present disclosure provides a method for detecting the concurrent presence of at least two targets within a biological sample. The method includes (a) contacting said biological sample with a first binding agent, said first binding agent operably linked to a first sortase molecule, wherein said first binding agent specifically binds to a first target; (b) contacting said biological sample with a second binding agent, said second binding agent operably linked to a first sortase recognition sequence peptide, wherein said second binding agent specifically binds to a second target; (c) adding a sortase substrate under conditions where a first sortase-mediated ligation of the sortase substrate to the first sortase recognition sequence will produce a ligation product, and (d) detecting the ligation product, wherein detection of said ligation product indicates the concurrent presence of the first target and the second target in the biological sample.

As used herein, by "sortase" or a "sortase molecule" is meant any member of the sortase family of enzymes. In some embodiments, a sortase molecule is a class A sortase or a class B sortase.

Sortase enzymes (also called sortases) are a class of Gram-positive bacterial enzymes that catalyze the transpeptidase reactions that covalently link certain cell surface proteins to the cell wall of the bacteria (see Cossart and Jonquieres, *Proc. Natl. Acad. Sci. USA* 97:5013-15, 2000; Maresso and Schneewind, Pharmacolog. Rev. 60: 128-141, 2008; Proft, *Biotechnol. Lett.* 32:1-10, 2010; Ton-That et al., *J. Biol. Chem.* 275:9876-81, 2000; Pritz et al., *J Org. Chem.* 72:3909-12, 2007; and Sakamoto et al., *Bioconjug Chem.* 21:2227-33, 2010). At least four different classes of sortase enzymes have been identified in Gram-positive bacteria, each with a distinct function and a different sortase recognition sequence. By "sortase recognition sequence" is meant an amino acid sequence that is recognized and cleaved by a sortase molecule, where the N-terminal portion of the cleaved sequence is then ligated by the sortase molecule to a sortase substrate. Class A enzymes (Sortase A or SrtA) are typically housekeeping sortases responsible for cell wall anchoring of proteins in the bacterium. The sortase recognition sequence for Sortase A is LPXTG (SEQ ID NO: 1) (where cleavage occurs between T and G). Class B enzymes (SrtB or Sortase B) often anchor proteins involved in iron acquisition to the cell wall. The sortase recognition sequence for Sortase B is NPQTN (SEQ ID NO: 2) or NPKTN (SEQ ID NO: 11) (where cleavage occurs between T and N; see Mazmanian et al., Proc. Natl. Acad. Sci. USA 99:2293-98, 2002; Hendrickx et al., 2011, Nat. Rev. Microbiol., 9:166-176) or NP(Q/K)(T/S)(N/G/S)(D/A) (SEQ ID NO: 23) (where cleavage occurs between (T/S) and (N/G/S); see Spirig et al., 2011, Mol. Microbiol, 82:1044-59). Class C enzymes (SrtC or Sortase C) (also known as subfamily 3 sortases) typically assemble pili on the surface of Gram-positive bacteria. The consensus sortase recognition sequence for class C sortases is (I/L)(P/A)XTG (SEQ ID NO: 6) (where cleavage occurs between T and G; reviewed in Hendrickx et al. *Nat Rev Microbiol.* 2011 9:166-76). Class D sortases (SrtD or Sortase D) (also known as subfamily 4 sortases) typically anchor proteins to cell wall peptidoglycan during sporulation. The sortase recognition sequence for additional class D sortases is LPNTA (SEQ ID NO: 7) (where cleavage occurs between T and A reviewed in Hendrickx et al. *Nat Rev Microbiol.* 2011 9:166-76). It should be noted that some publications interchange the designation of class C and class D sortases. In some embodiments, a sortase molecule of the disclosure is a class A sortase molecule or a class B sortase molecule. A database of sortase enzymes and proteins including sortase recognition sequences may be found on the World Wide Web at nihserver.mbi.ucla.edu/Sortase/.

Exemplary class A (subfamily 1) sortases can be found in *Bacillus anthracis* (NP_843215.1), *Bacillus cereus* (NP_830495.1), *Listeria innocua* (NP_470268.1), *Listeria monocytogenes* (NP_464454.1), *Staphylococcus aureus* (NP_375640.1; NP_373052.1, SEQ ID NO: 16), *Staphylococcus epidermidis* (NP_765631.1), *Streptococcus gordonii* (YP_001450517.1), and *Streptococcus pyogenes* (NP_802272.1).

An exemplary *S. aureus* class A sortase (NP_373052.1) has the amino acid sequence:

```
                                              (SEQ ID NO: 16)
MKKWTNRLMTIAGVVLILVAAYLFAKPHIDNYLHDKDKDEKIEQYDKNVK

EQASKDNKQQAKPQIPKDKSKVAGYIEIPDADIKEPVYPGPATPEQLNRG

VSFAEENESLDDQNISIAGHTFIDRPNYQFTNLKAAKKGSMVYFKVGNET

RKYKMTSIRDVKPTDVEVLDEQKGKDKQLTLITCDDYNEKTGVWEKRKIF

VATEVK
```

Exemplary class B sortases (subfamily 2) can be found in *B. anthracis* (NP_846988.1), *B. cereus* (NP_834250.1), *Bacillus halodurans* (NP_244160.1), *Clostridium difficile* (YP_001089230.1), *L. innocua* (NP_471617.1), *L. monocytogenes* (NP_465705.1), *S. aureus* (NP_374252.1), and *S. pyogenes* (YP_595846.1, SEQ ID NO: 17).

An exemplary *S. pyogenes* class B sortase (YP_595846.1) has the amino acid sequence:

```
                                              (SEQ ID NO: 17)
MISQRMMMTIVQVINKAIDTLILIFCLVVLFLAGFGLWDSYHLYQQADAS

NFKKFKTAQQQPKFEDLLALNEDVIGWLNIPGTHIDYPLVQGKTNLEYIN

KAVDGSVAMSGSLFLDTRNHNDFTDDYSLIYGHHMAGNAMFGEIPKFLKK

DFFNKHNKAIIETKERKKLTVTIFACLKTDAFDQLVFNPNAITNQDQQRQ

LVDYISKRSKQFKPVKLKHHTKFVAFSTCENFSTDNRVIVVGTIQE
```

Exemplary class C (subfamily 3) sortases can be found in *Actinomyces naeslundii* (AAC13546.1), *B. cereus* (NP_832268.1, SEQ ID NO: 18), *Clostridium perfringens* (NP_561073.1), *Lactococcus lactis* (NP_266915.1), and *S. pneumoniae* (NP_344986.1; NP_344987.1; NP_344988.1).

An exemplary *B. cereus* class C sortase (NP_832268.1) has the amino acid sequence:

```
                                              (SEQ ID NO: 18)
MKRNLVLGGIFLFGLGIFLYPTISNWLATRAHYSEISSYDKKIKALQKKE

VERREKEAAEYNKQVQTSTKTFTDPFSEKKSNHQAYADALNLGDVMGYIE

ISKINIKLPIYQGTSEEVLSRGIGHLDFSSLPVGGENTHTILTGHRGLPS

AKLFTDLDKLSKGDLFYLHSLDKVLAYKVDQIKVVLPHETDDLQIVQNKD

YTTLITCTPYGINTNRLLVRGERVELNEKEKQKVSTEIVIFNKWTVIVTI

LLLCVFLVEIYKKRFT
```

Exemplary class D (subfamilies 4 and 5) sortases can be found in *B. anthracis* (NP_847260.1), *B. cereus* (NP_830752.1; NP_834511.1; ZP_04265332.1, SEQ ID NO: 19), *B. halodurans* (NP_244463.1; NP_244878.1), *B. subtilis* (NP_388801.1), *Clostridium botulinum* (YP_001254630.1), *Geobacillus* sp. (YP_003672707.1), and *Oceanobacillus iheyensis* (NP_691253.1; NP_694114.1).

An exemplary *B. cereus* class D sortase (ZP_04265332.1) has the amino acid sequence:

(SEQ ID NO: 19)

```
MEKGKKVHKRKSKWILVIIGILVSIILFGFGIVAFFGWELTKQTALLAHT

VITPYKPVEQEKEFNQVWSKIPDPGEKLGELKFPSLSYEVPVVEGTHPKE

LESGVGHFAGSTLPGQGGNVVLSGHRNTSFRKLEDVKKGDQIKFATPYGE

FVYEITDFKITGAKDENIIVPTDYETLTLTTCYPFEYIGDAPDRFIVYTK

IVSKPDLKKQS
```

By "sortase substrate" is meant a composition (e.g., a peptide) comprising a poly-glycine motif where the poly-glycine motif comprises three adjacent glycine residues, joined to one another by peptide bonds, or four adjacent glycine residues, joined to one another by peptide bonds, or five adjacent glycine residues, joined to one another by peptide bonds, or more than five adjacent glycine residues, joined to one another by peptide bonds. A poly-glycine motif can be on its own in a short peptide (e.g., a peptide comprising the sequence N-terminus-GGG-C-terminus) or can be incorporated into a larger molecule (e.g., a GGG-comprising polypeptide such as a GGG-antigen as described herein). In some embodiments, the sortase substrate includes or is operably linked to a detectable moiety. Multiple suitable detectable moieties are known, and the detectable moiety can include, without limitation, an antigen, hapten, member of a binding pair (e.g., see Table 1), enzyme (e.g., a reporter enzyme such as peroxidase), radioactive nuclide, or a fluorescent moiety (e.g., a fluorophore or nanodot).

Class A and class B sortases ligate the carboxyl-group of the C-terminal amino acid of their cleaved recognition sequence to the amino-group of one of the glycine residues in the poly-glycine motif, and class C and class D sortases can act in the same way. Thus, since sortase A cleaves between the T and the G in its sortase recognition sequence, the sortase A ligation product with a sortase substrate comprising three adjacent glycines will have the sequence: N-terminus LPXT-GGG-C-terminus (where X is any amino acid) (SEQ ID NO: 8). Since sortase B cleaves between the T and the N in its sortase recognition sequence, the sortase B ligation product with a sortase substrate comprising three adjacent glycines will have the sequence: N-terminus NPQT-GGG-C-terminus (SEQ ID NO: 9).

Since sortase C (i.e., class C sortase) cleaves between the T and the G in its sortase recognition sequence, the sortase C ligation product with a sortase substrate comprising three adjacent glycines will have the sequence: N-terminus (I/L) (P/A)XT-GGG-C-terminus (SEQ ID NO: 10). Finally, since sortase D cleaves between the T and the A in its sortase recognition sequence, the sortase D ligation product with a sortase substrate comprising three adjacent glycines will have the sequence: N-terminus LPNT-GGG-C-terminus (SEQ ID NO: 12).

The methods and compositions of the disclosure utilize this ligation feature of the sortase enzymes to detect co-expression of two molecules in a biological sample. An embodiment of a non-limiting method of the present disclosure is depicted schematically in FIG. 1. As shown in FIG. 1 (left side), two target-specific antibodies are employed, where the Target 1-specific antibody operably linked to a sortase recognition sequence (in this case the Sortase A recognition sequence comprising the sequence LPXTG (SEQ ID NO: 1)) and the Target 2-specific antibody operably linked to a biologically active fragment of Sortase A. If both Target 1 and Target 2 are present in the biological sample, both antibodies will specifically bind their targets. Following washing to remove unbound antibody, a sortase substrate (i.e., a poly-glycine motif-bearing molecule) is added. To facilitate detection, in the example depicted in FIG. 1, the sortase substrate is operably linked to an antigen. If both Target 1 and Target 2 are present, the active Sortase A on the Target 2-specific antibody will cleave the sortase recognition sequence between the T and G residue and then ligate the LPXT portion of the sortase recognition sequence still operably linked to the Target 1-specific antibody to the sortase substrate. The resulting ligation product, which remains operably linked to the Target 1-specific antibody following washing to remove any unbound poly-glycine motif-bearing molecule, can then be detected by a third antibody (which is detectable in this example, hence depicted as "DA" in FIG. 1) that specifically binds to the antigen operably linked to the sortase substrate.

In some embodiments, the methods and compositions disclosed herein provide for enhancement of specificity of detection by the requirement that both targets need to be engaged for efficient ligation of the sortase substrate to the sortase recognition sequence to occur, such that specific binding of either only the SrtA-conjugated antibody or only the LPXTG-conjugated antibody to their respective targets will not efficiently trigger ligation-specific binding of both antibodies is needed for ligation. In some embodiments, further control of SrtA activity (e.g., to reduce precocious ligation) can be implemented using inhibitors of SrtA activity. Such inhibitors are known and include, without limitation, 1-(3,4-dichlorophenyl)-3-(dimethylamino)-1-propanone hydrochloride (commercially available, for example, from ChemBridge Corp., San Diego, Calif.; see Cat. No. 5927943) (see also, e.g., Mazmanian S. K. et al., *Proc. Natl. Acad. Sci. USA* 99:4 2293-2298, 2002).

The advantages of the present disclosure include at least the following. First, the present disclosure is versatile with respect to the mode of detection. For example, the methods and compositions of the invention can be adapted for colorimetric, luminescence or fluorescence types of detectable moieties. Further, target-independent effects are precisely controlled by virtue of the fact that engagement of both targets by the corresponding modified antibodies is absolutely required for ligation of the poly-glycine motif-bearing molecule to occur.

The present disclosure also contemplates the use of additional sortase enzymes to confirm the concurrent presence of more than two targets within a biological sample.

Accordingly, in another aspect, the present disclosure provides a method for detecting the concurrent presence of at least three targets within a biological sample. The method includes (a) contacting said biological sample with a first binding agent, said first binding agent operably linked to a first sortase molecule, wherein said first binding agent specifically binds to a first target; (b) contacting said biological sample with a second binding agent, said second binding agent operably linked to a first sortase recognition sequence peptide, wherein said second binding agent specifically binds to a second target; (c) contacting said biological sample with a third binding agent, said third binding agent operably linked to a second sortase molecule; (d) adding an intermediate reagent comprising a sortase substrate conjugated to a second sortase recognition sequence peptide under conditions where a first sortase-mediated ligation of the intermediate reagent to the first sortase recognition sequence will produce an intermediate product, (e) adding a sortase substrate under conditions where a second sortase-mediated ligation of the sortase substrate to the second sortase recognition sequence peptide on the intermediate product will produce a ligation product, and (f) detecting the second ligation product, wherein detection of said ligation product indicates the concurrent presence of the first target, the second target, and the third target in the biological sample.

Figure 2:
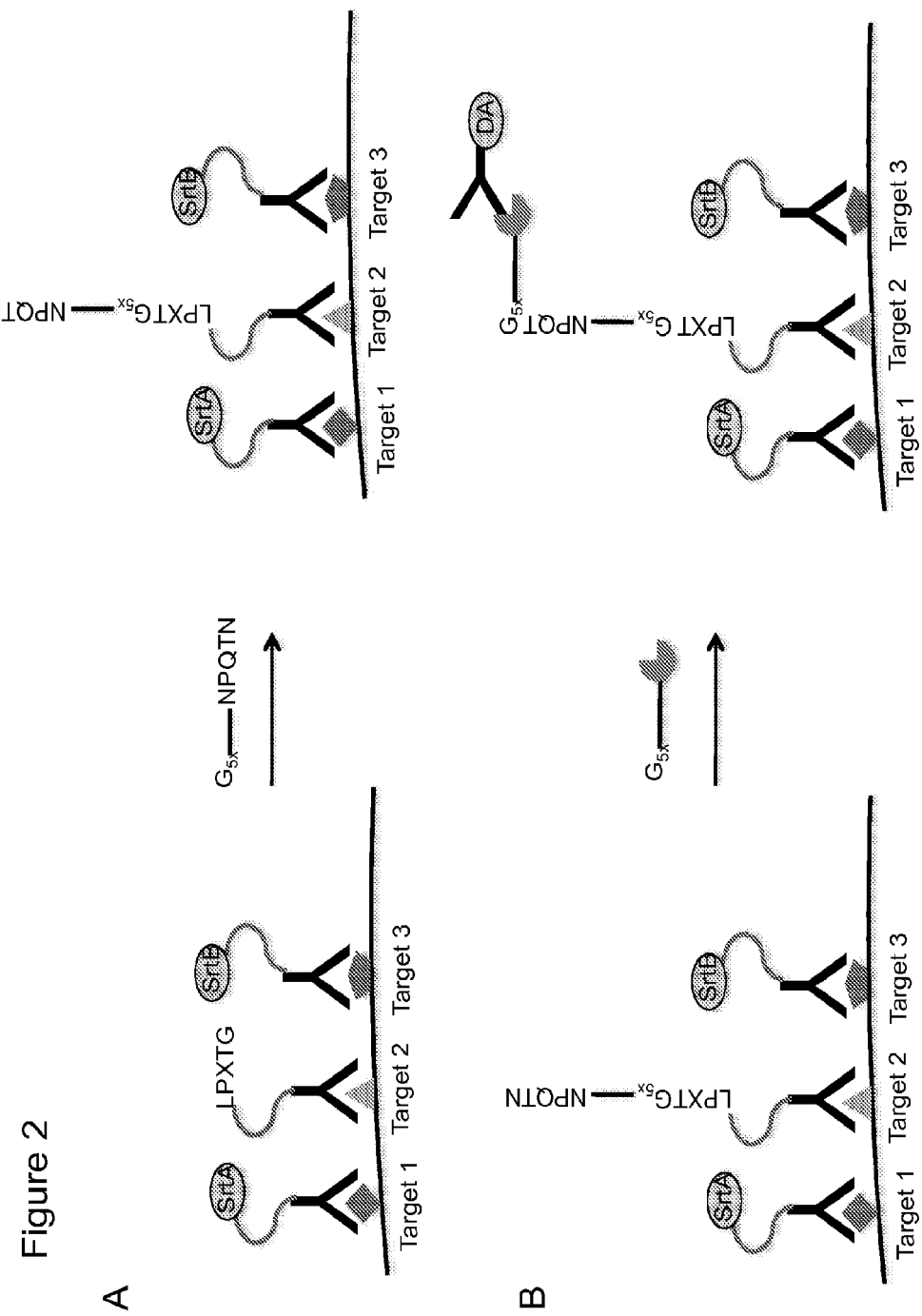
FIG. 2 is a schematic representation showing a non-limiting multiplex embodiment of the present disclosure using additional sortases. In this example, three modified antibodies (each to distinct biological targets) are used, consisting of the following antibodies: the SrtA-attached antibody specifically binds to Target 1; LPXTG sequence-attached antibody specifically binds to Target 2, and SrtB-attached antibody specifically binds to Target 3. The assay depicted in this Figure can be conducted by first allowing the three antibodies to bind to their respective targets. After removal of unbound antibodies through washing steps, the poly-glycine peptide bearing a SrtB recognition sequence NPQTN (SEQ ID NO: 2) is incubated to allow for ligation of this peptide to the LPXTG-attached antibody by the SrtA activity of the SrtA-attached antibody. This is followed by repeated washing to remove any unbound $G_{5x}$NPQTN peptides, followed by incubation with the poly-glycine peptide fused to the antigen, which can then be detected.

This non-limiting aspect of the disclosure, which is depicted schematically in FIG. 2, utilizes a first, second, and a third modified antibody species, each recognizing a unique target suspected of being expressed within a biological sample. Operably linked to the first antibody species (i.e., the antibody that specifically binds to Target 1) is the sortase A (SrtA) enzyme (or biologically active fragment thereof). Operably linked to the second species (i.e., the antibody that specifically binds to Target 2) is the LPXTG (SEQ ID NO: 1) recognition sequence for SrtA-mediated molecular ligation. Finally, operably linked to the third antibody species (i.e., the antibody that specifically binds to Target 3) is the sortase B (SrtB) enzyme or biologically active fragment thereof (see Mazmanian et al., *Proc. Natl. Acad. Sci. USA* 99:2293-98, 2002). As shown in FIG. 2, in a first step, the three modified antibody species (i.e., modified by being operably linked to sortase A, sortase B, or the sortase A recognition sequence) would be allowed to bind to their respective targets within a biological sample. Addition of a sortase substrate operably linked to the sequence NPQTN (SEQ ID NO: 2) (NPQTN is the Sortase B recognition sequence) would result in the SrtA-mediated ligation of the sortase substrate-NPQTN molecule to the antibody that specifically binds to Target 2. To prevent SrtA from re-cleaving this initial ligation product mediated by Sortase A, a Sortase A specific irreversible inhibitor can be used. Such inhibitors have been previously described (see Scott C. J. et al., *Biochem. J.* 366, 953-958, 2002). After washing to remove any unbound sortase substrate operably linked to the sequence NPQTN (SEQ ID NO: 2), the subsequent addition of a sortase substrate (which, in this example is operably linked to an antigen depicted as a ¾ circle shape in FIG. 2) would result in the SrtB-mediated ligation of the sortase substrate operably linked to an antigen to the antibody that specifically binds to Target 2. Subsequent detection of the ligation product comprising LPXT-polyG-NPQT-polyG-antigen will indicate the concurrent presence of all three targets within the sample (see FIG. 2).

It should be noted that in the examples depicted in FIGS. 1 and 2, the antibodies that specifically bind the final ligation product are depicted as specifically binding the antigen. Such is not a requirement; of course. For example, an antibody or other binding agent that specifically binds a peptide comprising the sequence LPXTGGGGG (SEQ ID NO: 13) (for the example of FIG. 1) or the sequence NPQTGGGGG (SEQ ID NO: 14) (for the example of FIG. 2) can also be employed. In some embodiments, the antibody or binding agent that specifically binds the ligation product is detectable.

In another aspect, a variety of sortase enzymes can be operably linked to various binding agents, and their sortase recognition sequences can be operably linked to various binding agents and/or sortase substrates as in FIG. 2. Thus, the present disclosure contemplates the detection of concurrent expression of multiple targets in a biological sample utilizing the various sortase molecules and their sortase recognition sequences.

In certain embodiments, a spacer comprising amino acid sequence or other molecule of variable lengths can be used between the binding agent (e.g., an antibody) and the sortase molecule or the sortase recognition sequence (i.e., the LPXTG motif (SEQ ID NO: 1) for Sortase A). The length of the spacer can be varied to modulate the effective range between the two binding agents to achieve efficient sortase reactivity. The sortase and sortase recognition sequence modified binding agents can be generated by gene fusion or bioorthogonal conjugation methodologies.

As used herein, by "target" is meant anything that can be specifically bound by an binding agent as disclosed herein. A target may be itself a molecule (e.g., the MET kinase is a target of a MET kinase-specific antibody). A target may also be an epitope or fragment on a molecule (e.g., a fragment of ALK kinase comprising a phosphorylated tyrosine at position 1078 is the target of a Phospho-ALK (Tyr1078)-specific antibody). A target may be as small as a few atoms (e.g., a phosphorylated tyrosine residue is a target of a phosphorylated tyrosine-specific antibody (e.g., the 4G10 antibody commercially available from many sources including EMD Millipore, Billerica, Mass.)). Two targets may be on the same molecule (e.g., a first target of phosphorylated tyrosine at position 1078 on ALK kinase and a second target of phosphorylated tyrosine at position 1278 on ALK kinase) or can be on different molecules (e.g., a first target of ALK kinase and a second target of Akt kinase).

As used herein, by the term "molecule" is meant any chemical including, without limitation, polypeptides (e.g., antibodies or fusion proteins), nucleic acid molecules (e.g., DNA or RNA), peptides, carbohydrates, lectins, lipids, fatty acids, polysaccharides, or any modifications of the above (e.g., glycoproteins, peptide nucleic acids).

As used herein, by the term "binding agent" is meant any molecule (including, without limitation, an antibody, a fusion protein, a lectin, or a nucleic acid molecule (e.g., a nucleic acid aptamer)) that is able to specifically bind to a target.

As used herein, by "specifically binding" or "specifically binds" means that a binding agent that may be used in the various methods of the disclosure interacts with its target, where the interaction is dependent upon the presence of a particular structure (e.g., the antigenic determinant or epitope on the polypeptide or the nucleotide sequence of the polynucleotide); in other words, the reagent is recognizing and binding to a specific polypeptide or polynucleotide structure rather than to all polypeptides or polynucleotides in general.

A binding agent that specifically binds to the target may be referred to as a target-specific binding agent or an anti-target binding agent. For example, an antibody that specifically binds to an AKT polypeptide may be referred to as an AKT-specific antibody or an anti-AKT antibody.

In some embodiments, a binding agent that specifically binds its target has a binding affinity ($K_D$) for its target of $1 \times 10^{-6}$ M or less. In some embodiments, a binding agent that specifically binds to its target binds to its target with a $K_D$ of $1 \times 10^{-7}$ M or less, or a $K_D$ of $1 \times 10^{-8}$ M or less, or a $K_D$ of $1 \times 10^{-9}$ M or less, or a $K_D$ of $1 \times 10^{-10}$ M or less, of a $K_D$ of $1 \times 10^{-11}$ M or less, of a $K_D$ of $1 \times 10^{-12}$ M or less. In certain embodiments, a binding agent that specifically binds to its target binds to its target with a $K_D$ of 1 pM to 500 pM, or between 500 pM to 1 µM, or between 1 µM to 100 nM, or between 100 mM to 10 nM.

In some embodiments, the binding agent used in the various methods and compositions of the disclosure are antibodies. It shall be understood, of course, that just because one binding agent (e.g., that specifically binds to Target 1) is an antibody does not mean that the second binding agent (e.g., that specifically binds to Target 2) is necessarily also antibody. For example, the binding agent that specifically binds to Target 1 may be an antibody and the binding that specifically binds to Target 2 may be a small molecule that specifically binds to Target 2 (e.g., if Target 2 is the ALK kinase, the binding agent may be the small molecule crizotinib (also known as PF-02341066; see U.S. Pub. No. 2008/0300273) or the small molecule TAE-684 (see Galkin, et al., Proc. National Acad. Sci. 104(1) 270-275, 2007)

The term "antibody" or "antibodies" refers to all types of immunoglobulins, including IgG, IgM, IgA, IgD, and IgE, including binding fragments thereof (i.e., fragments of an antibody that are capable of specifically binding to the antibody's target, such as $F_{ab}$, and $F(ab')_2$ fragments), as well as recombinant, humanized, polyclonal, and monoclonal antibodies and/or binding fragments thereof. Antibodies can be derived from any species of animal, such as from a mammal. Non-limiting exemplary natural antibodies include antibodies derived from human, chicken, goats, and rodents (e.g., rats, mice, hamsters and rabbits), including transgenic rodents genetically engineered to produce human antibodies (see, e.g., Lonberg et al., WO93/12227; U.S. Pat. No. 5,545,806; and Kucherlapati, et al., WO91/10741; U.S. Pat. No. 6,150,584, which are herein incorporated by reference in their entirety). Antibodies may be also be chimeric antibodies. See, e.g., M. Walker et al., *Molec. Immunol.* 26: 403-11 (1989); Morrision et al., *Proc. Nat'l. Acad. Sci.* 81: 6851 (1984); Neuberger et al., *Nature* 312: 604 (1984)). The antibodies may be recombinant monoclonal antibodies produced according to known methods (see, e.g., U.S. Pat. Nos. 4,474,893; 4,816,567; 7,485,291, and US Patent Publication No. 20110045534). The antibodies may also be chemically constructed specific antibodies made according to the method disclosed in U.S. Pat. No. 4,676,980.

Natural antibodies are the antibodies produced by a host animal, however the disclosure also contemplates the use of genetically altered antibodies wherein the amino acid sequence has been varied from that of a native antibody. Because of the relevance of recombinant DNA techniques to this application, one need not be confined to the sequences of amino acids found in natural antibodies; antibodies can be redesigned using recombinant methods to obtain desired characteristics.

Thus, recombinant antibodies are also included in the present disclosure. In some embodiments, recombinant antibodies have the same amino acid sequence as the natural antibodies or have altered amino acid sequences of the natural antibodies. They can be made in any expression systems including both prokaryotic and eukaryotic expression systems or using phage display methods (see, e.g., Dower et al., WO91/17271 and McCafferty et al., WO92/01047; U.S. Pat. No. 5,969,108, which are herein incorporated by reference in their entirety). Antibodies can be engineered in numerous ways. They can be made as single-chain antibodies (including small modular immunopharmaceuticals or SMIPs™), Fab and $F(ab)_2$ fragments, etc. Antibodies can be humanized, chimerized, deimmunized, or fully human. Numerous publications set forth the many types of antibodies and the methods of engineering such antibodies. For example, see U.S. Pat. Nos. 6,355,245; 6,180,370; 5,693,762; 6,407,213; 6,548,640; 5,565,332; 5,225,539; 6,103,889; and 5,260,203. The genetically altered antibodies may be functionally equivalent to the above-mentioned natural antibodies. In certain embodiments, modified antibodies can provide improved stability or/and therapeutic efficacy.

Non-limiting examples of modified antibodies include those with conservative substitutions of amino acid residues, and one or more deletions or additions of amino acids that do not significantly deleteriously alter the antigen binding utility. Substitutions can range from changing or modifying one or more amino acid residues to complete redesign of a region as long as the binding specificity is maintained. Antibodies can be modified post-translationally (e.g., acetylation, and/or phosphorylation) or can be modified synthetically (e.g., operably linked to a detectable moiety). Antibodies with engineered or variant constant or Fc regions can be useful in modulating effector functions, such as, for example, antigen-dependent cytotoxicity (ADCC) and complement-dependent cytotoxicity (CDC). The Fc regions of antibodies can also be modified to be operably linked to peptides comprising a poly-glycine motif sequence or a sortase recognition sequence (e.g., LPXTG (SEQ ID NO: 1), NPQTN (SEQ ID NO: 2), LPNTA (SEQ ID NO: 7), or LPNTG (SEQ ID NO: 15).

Also contemplated within the present disclosure are antibody molecules with fewer than 4 chains, including single chain antibodies, Camelid antibodies and the like and components of an antibody, including a heavy chain or a light chain. In some embodiments an immunoglobulin chain may comprise in order from 5' to 3', a variable region and a constant region. The variable region may comprise three complementarity determining regions (CDRs), with interspersed framework (FR) regions for a structure FR1, CDR1, FR2, CDR2, FR3, CDR3 and FR4. Also within the disclosure are heavy or light chain variable regions, framework regions and CDRs. An antibody may comprise a heavy chain constant region that comprises some or all of a CH1 region, hinge, CH2 and CH3 region.

Humanized antibodies are also included as types of antibodies useful in the various methods and compositions disclosed herein. The term "humanized antibody", as used herein, refers to antibody molecules in which amino acids have been replaced in the non-antigen binding regions in order to more closely resemble a human antibody, while still retaining the original binding ability. Other antibodies specifically contemplated are oligoclonal antibodies. As used herein, the phrase "oligoclonal antibodies" refers to a predetermined mixture of distinct monoclonal antibodies. See, e.g., PCT publication WO 95/20401; U.S. Pat. Nos. 5,789, 208 and 6,335,163. In one embodiment, oligoclonal antibodies consisting of a predetermined mixture of antibodies against one or more epitopes are generated in a single cell. In other embodiments, oligoclonal antibodies comprise a plurality of heavy chains capable of pairing with a common light chain to generate antibodies with multiple specificities (e.g., PCT publication WO 04/009618). Oligoclonal antibodies are particularly useful when it is desired to target multiple epitopes on a single target. In view of the assays and epitopes disclosed herein, those skilled in the art can generate or select antibodies or mixtures of antibodies that are applicable for an intended purpose and desired need.

Polyclonal antibodies useful in practicing the methods disclosed herein may be produced according to standard techniques by immunizing a suitable animal (e.g., rabbit, goat, etc.) with an antigen encompassing a desired epitope (e.g. the fusion junction between the ALK portion and the portion of the second fusion partner present in the ALK fusion polypeptide), collecting immune serum from the animal, and separating the polyclonal antibodies from the immune serum, and purifying polyclonal antibodies having the desired specificity, in accordance with known procedures. The antigen may be a synthetic peptide antigen comprising the desired epitopic sequence, selected and constructed in accordance with well-known techniques. See, e.g., ANTIBODIES: A LABORATORY MANUAL, Chapter 5, p. 75-76, Harlow & Lane Eds., Cold Spring Harbor Laboratory (1988); Czernik, *Methods In Enzymology*, 201: 264-283 (1991); Merrifield, *J. Am. Chem. Soc.* 85: 21-49 (1962)).

Polyclonal antibodies produced as described herein may be screened and isolated as further described below.

Monoclonal antibodies may also be beneficially employed in the methods of the disclosure, and may be produced in hybridoma cell lines according to the well-known technique of Kohler and Milstein. *Nature* 265: 495-97 (1975); Kohler and Milstein, *Eur. J. Immunol.* 6: 511 (1976); see also, CURRENT PROTOCOLS IN MOLECULAR BIOLOGY, Ausubel et al. Eds. (Wiley and Sins, New York, N.Y. 1989 and yearly updates up to and including 2010). Monoclonal antibodies so produced are highly specific, and can improve the selectivity and specificity of assay methods disclosed herein. For example, a solution containing the appropriate antigen (e.g. a synthetic peptide comprising the fusion junction of the ALK portion and the portion of the second fusion partner present in the ALK fusion polypeptide) may be injected into a mouse and, after a sufficient time (in keeping with conventional techniques), the mouse sacrificed and spleen cells obtained. The spleen cells are then immortalized by fusing them with myeloma cells, typically in the presence of polyethylene glycol, to produce hybridoma cells. Rabbit fusion hybridomas, for example, may be produced as described in U.S. Pat. No. 5,675,063. The hybridoma cells are then grown in a suitable selection media, such as hypoxanthine-aminopterin-thymidine (HAT), and the supernatant screened for monoclonal antibodies having the desired specificity, as described below. The secreted antibody may be recovered from tissue culture supernatant by conventional methods such as precipitation, ion exchange or affinity chromatography, or the like.

Monoclonal Fab fragments may also be produced in *Escherichia coli* by recombinant techniques known to those skilled in the art. See, e.g., W. Huse, *Science* 246: 1275-81 (1989); Mullinax et al., *Proc. Nat'l Acad. Sci.* 87: 8095 (1990). If monoclonal antibodies of one isotype are desired for a particular application, particular isotypes can be prepared directly, by selecting from the initial fusion, or prepared secondarily, from a parental hybridoma secreting a monoclonal antibody of different isotype by using the sib selection technique to isolate class-switch variants (Steplewski, et al., *Proc. Nat'l. Acad. Sci.*, 82: 8653 (1985); Spira et al., *J. Immunol. Methods*, 74: 307 (1984)). The antigen combining site of the monoclonal antibody can be cloned by PCR and single-chain antibodies produced as phage-displayed recombinant antibodies or soluble antibodies in *E. coli* (see, e.g., ANTIBODY ENGINEERING PROTOCOLS, 1995, Humana Press, Sudhir Paul editor.)

Further still, U.S. Pat. No. 5,194,392, Geysen (1990) describes a general method of detecting or determining the sequence of monomers (amino acids or other compounds) which is a topological equivalent of the epitope (i.e., a "mimotope") which is complementary to a particular paratope (antigen binding site) of an antibody of interest. More generally, this method involves detecting or determining a sequence of monomers which is a topographical equivalent of a ligand which is complementary to the ligand binding site of a particular receptor of interest. Similarly, U.S. Pat. No. 5,480,971, Houghten et al. (1996) discloses linear $C_1$—C-alkyl peralkylated oligopeptides and sets and libraries of such peptides, as well as methods for using such oligopeptide sets and libraries for determining the sequence of a peralkylated oligopeptide that preferentially binds to an acceptor molecule of interest. Thus, non-peptide analogs of the epitope-bearing peptides also can be made routinely by these methods.

Antibodies useful in the methods disclosed herein, whether polyclonal or monoclonal, may be screened for specificity according to standard techniques. See, e.g., Czernik et al., *Methods in Enzymology*, 201: 264-283 (1991). For example, the antibodies may be screened against a peptide library by ELISA to ensure specificity for the desired antigen or epitope thereof. The antibodies may also be tested by western blotting against cell preparations containing target protein to confirm reactivity with the only the desired target and to ensure no appreciable binding to other proteins or other biomolecules (e.g., lectins, lipids, carbohydrates, etc.).

Antibodies and other binding agents employed in the methods disclosed herein may be further characterized by, and validated for, use in a particular assay format, for example flow cytometry (FC), immunohistochemistry (IHC), and/or immunocytochemistry (ICC). Such methods are further described herein. The antibodies described herein, used alone or in the below-described assays, may also be advantageously operably linked to (e.g., labeled with) detectable moieties such as fluorescent dyes (e.g. Alexa488, phycoerythrin), or labels such as quantum dots, for use in multi-parametric analyses along with other signal transduction (phospho-AKT, phospho-Erk 1/2) and/or cell marker (cytokeratin) antibodies.

As used herein, by "operably linked" is meant that one molecule (e.g., a sortase molecule) is attached to a second molecule (e.g., a binding agent) such that both molecules are functional. For example, a binding agent operably linked to a sortase molecule retains its ability to specifically bind the target specifically bound by the binding agent and also retains the biological activity of the sortase molecule to cleave and ligate its sortase recognition sequence to a sortase substrate. Similarly, a binding agent operably linked to a detectable moiety retains its ability to specifically bind the target specifically bound by the binding agent and also retains its ability to be detectable by the presence of the detectable moiety. The two molecules operably linked to one another may be directly attached to one another by a covalent or non-covalent (e.g., van der Waals bond or hydrogen bond) bond, or may be indirectly attached to one another. For example, for operable linkage via indirectly attachment of a detectable moiety, a binding agent can be biotinylated (e.g., using the EZ-Link Sulfo-NHS kit commercially available from Thermo Fisher Scientific, Rockland, Ill.), and can thus be detected using detectable streptavidin (which specifically binds to biotin). Methods for attaching detectable moieties to molecules (e.g., to the binding agents described herein) are well known.

Additional binding agents of the disclosure include, without limitation, protein binding domains or nucleic acid aptamers, which bind, in a fusion-protein or truncated-protein specific manner, to essentially the same epitope to which a polypeptide with kinase activity-specific antibody useful in the methods of the invention binds. See, e.g., Neuberger et al., *Nature* 312: 604 (1984). Such equivalent non-antibody reagents may be suitably employed in the methods further described below.

In some embodiments, the binding agents that are operably linked to a molecule (e.g., a sortase recognition sequence or a sortase molecule) are directly attached to the molecule. To generate such binding agents directly attached to a molecule (e.g., a sortase molecule or a sortase recognition sequence), standard molecular biology methods can be employed. For example, to generate an antibody operably linked via direct attachment to a sortase recognition sequence (e.g., leucine-proline-any amino acid residue-threonine-glycine), the nucleic acid sequence encoding the heavy chain of an antibody that specifically binds to a desired target can be engineered using recombinant molecular biology techniques to include nucleotide sequence encoding LPXTG (SEQ ID NO: 1) just prior to the stop codon at the 3' end of the nucleic acid sequence. As the heavy chain is expressed such that the constant region is at the C-terminal end of the chain, this modification would simply add a peptide comprising the sequence LPXTG (SEQ ID NO: 1) at the C-terminus of the constant region of the heavy chain. A similar modification can, of course, be made to the light chain of an antibody.

To generate an antibody operably linked via direct attachment to a sortase molecule, a biologically active fragment of a sortase molecule of interest (e.g., Sortase A, Sortase B, Sortase C, or Sortase D) can be similarly generated using recombinant molecular biology techniques.

As described below in the examples, the entire amino acid sequence of a sortase molecule need not be operably linked to a binding agent that specifically binds to one of the two targets suspected of being present in the biological sample. Only a fragment that is biologically active (i.e., retains the sortase molecule's ability to ligate) is required.

In further embodiments, direct attachment of a sortase molecule or a sortase recognition sequence (or another moiety such as a myc-tag or a biotin moiety) can be accomplished by chemical conjugation. Several commercially available kits can be used to modify the binding agents that specifically bind to targets to be directly attached to a moiety (e.g., a sortase molecule or a sortase recognition sequence). For example, Solulink, Inc. (San Diego, Calif.) sells kits and reagents that can be used to covalently conjugate two molecules (e.g., a sortase molecule and a binding agent) to one another. Using the Solulink kit sold as catalog no. S-9010-1 (from Solulink, Inc., San Diego, Calif.), for example, a primary amine group or lysine of a binding agent (e.g., a primary amine or lysine on the Fc portion of an antibody) is conjugated to the S-HyNic (succinimidyl-6-hydrazino-nicotinamide) linker and a primary amino or lysine on the sortase molecule can be conjugated to the S-4FB (succinimidyl-4-formylbenzamide) linker. The binding agent and the sortase molecule are then incubated together to covalently conjugate the binding agent to the sortase molecule. Of course, the linkers can be interchanged (e.g., the S-HyNic linker can be conjugated, to the sortase molecule and the S-4FB linker can be conjugated to the binding agent.

As discussed above, in various embodiments, the modified binding agents may be operably linked to another molecule (e.g., a sortase molecule or a sortase recognition sequence) by direct attachment or indirect attachment. As described above, direct attachment is fairly straight forward and can be accomplished by, for example, using recombinant biology techniques to fuse a nucleic acid sequence encoding the binding agent with a nucleic acid sequence encoding, for example, a sortase recognition sequence. The resulting nucleic acid molecule can be cloned into any standard expression vector (e.g., the cDNA3 vector commercially available from Invitrogen, Inc. (a Life Technologies company), Carlsbad, Calif.) and the encoded protein expressed in any standard expression cell (e.g., CHO cells, COS cells, HeLa cells, etc., all of which are commercially available from the American Type Culture Collection, Manassas, Va.).

In various embodiments, the binding agents may be modified by being operably linked to another molecule (e.g., a sortase molecule) by indirect attachment. To do this, binding member pairs can be utilized, where one molecule (e.g., a binding agent) is directly attached to one member of the binding member pair and the other molecule (e.g., a sortase molecule) is directly attached to a second member of the binding member pair. Of course, either of the two molecules (i.e., the binding agent or the sortase molecule) can itself be indirectly attached to one of the two members of a binding member pair via an indirect attachment by utilizing a second binding member pair.

As used herein, by "binding member pair" is meant any two molecules that are specifically bind to one another. Each of these two molecules is called a member of that binding member pair. Table 1 provides a non-limiting list of binding member pairs that can be utilized in the methods of the various embodiments of the disclosure, and a reference describing the binding member pair (the entire teachings of which are hereby incorporated by reference).

TABLE 1

| Binding Member Pair | First Member | Second Member | Reference |
| --- | --- | --- | --- |
| Antibody/antigen | Antibody | Antigen | |
| Avidin/biotin | Avidin (or modifications thereof including neutravidin) | biotin | |
| Streptavidin/biotin | Streptavidin | biotin | |
| Strep-tag/Strep-tactin | Strep-tag | Strep-tactin | Schmidt and Skerra, Nature Protocols 2: 1528-1535, 2007; Skerra and Schmidt, Methods Enzymol 326: 271-304, 2000; U.S. Pat. No. 5,506,121 |
| GST (glutathione S-transferase)/glutathione | GST | glutathione | U.S. Pat. No. 5,654,176 |
| His tag (i.e., 2-6 adjacent histidine residues)/divalent metal ion (e.g., Nickel or Cobalt ion) | His tag (e.g., $H_2$, $H_3$, $H_4$, $H_5$, or $H_6$) | Divalent metal ion (e.g., Ni-NTA) | U.S. Pat. No. 4,569,794 |
| Flag tag/anti-FLAG antibody | FLAG tag (i.e., DYKDDDDK (SEQ ID NO: 22) | Antibody that specifically binds DYKDDDDK (SEQ ID NO: 22) | |

A classic binding member pair is an antibody and the antigen to which the antibody specifically binds. That antigen may even be the Fc portion of another antibody. For example, it is common in biology to use primary and secondary antibodies, where the primary antibody specifically binds to the target of interest and the secondary antibody specifically binds to the constant region of the primary antibody. For example, if the primary antibody is a murine monoclonal antibody, the secondary antibody can be a polyclonal antibody that specifically binds to all mouse antibodies.

Of course where the binding member pair is an antigen/antibody pair, any number of art-known tags or epitopes can be used. Table 1 lists just one example of this (i.e., a Flag tag and an anti-FLAG antibody), but additional tags (and their specific antibodies) can be used including, without limitation, a HIS tag, a myc tag, a hemaggluinin tag (i.e., an HA tag), an HSV tag, a V5 tag, or a VSV-G tag. Any of these tags can be attached to the antibody that specifically binds to a target and the anti-tag antibody that specifically binds to that tag can be attached a sortase molecule or a sortase recognition sequence.

Figure 3:
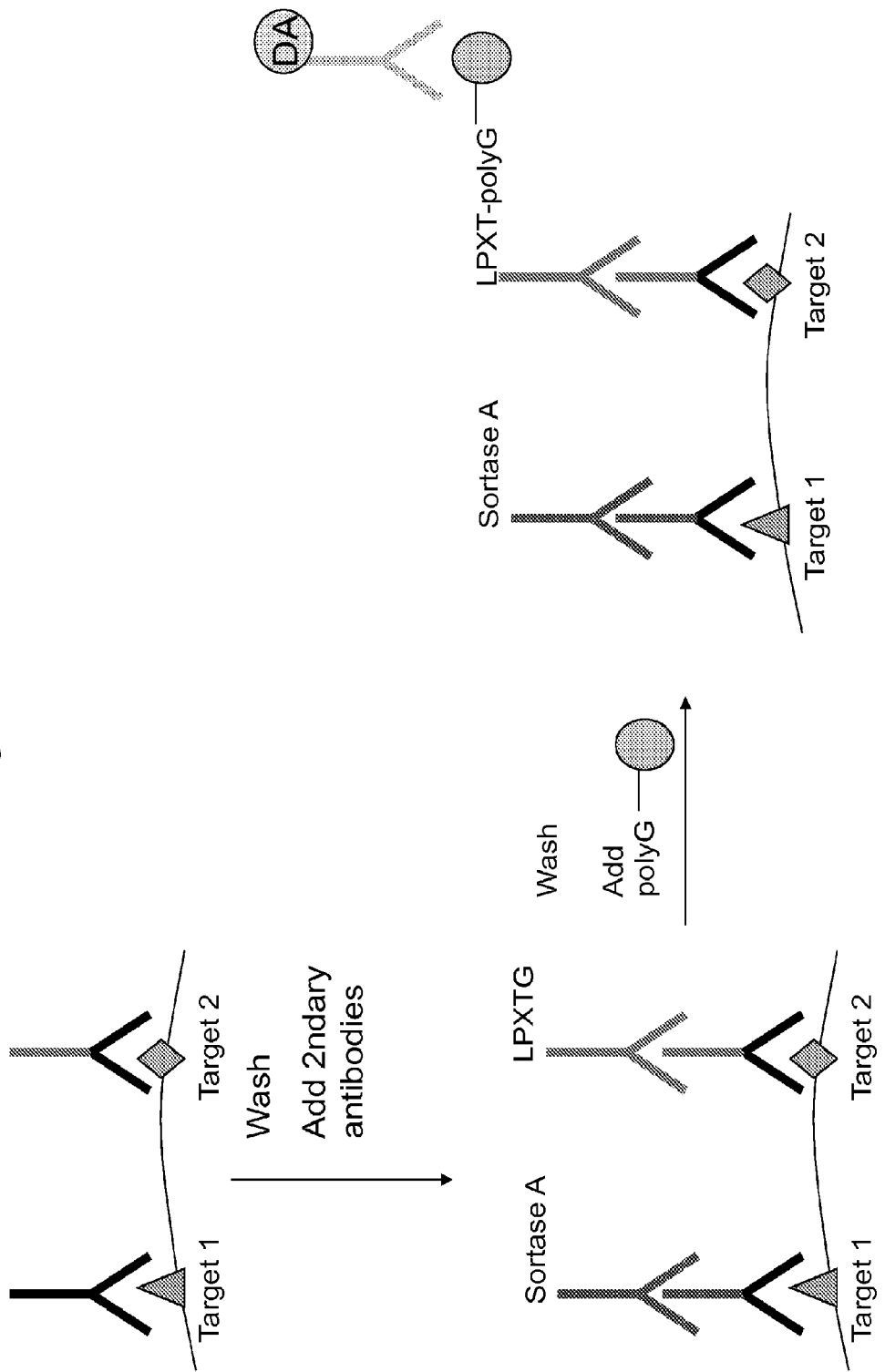
FIG. 3 is a schematic representation of a non-limiting embodiment of the present disclosure using secondary antibodies.

A non-limiting example of this embodiment of the present disclosure is depicted in FIG. 3. In FIG. 3, the antibody that specifically binds to Target 1 is a rabbit antibody (denoted by the blue "stem" of the antibody) while the antibody that specifically binds to Target 2 is a murine antibody (denoted by the red "stem" of the antibody). After washing to remove unbound primary antibody, secondary antibodies are added. The anti-rabbit antibody is directly attached to sortase A while the anti-mouse antibody is directly attached to the sortase A recognition sequence. After washing and adding the sortase substrate attached to an antigen (blue oval), the ligation product can be detected using a detectable antibody that specifically binds to the antigen. Since the primary antibody is still bound to Target 2 and since the secondary anti-mouse antibody is still bound to the primary antibody, the anti-antigen detectable antibody will remain bound to the biological sample.

Members of binding member pairs can also be attached to molecules using known methods. Indeed, some methods are commercially available. For example, the streptavidin/biotin binding member pair can be utilized to generate a binding agent operably linked to a sortase A recognition sequence as follows: One of the many biotinylation kits commercially available from Thermo Scientific (e.g., the EZ-Link NHS PEG4 Biotin kit or the EZ-Link Sulfo-NHS-LC-Biotin kit) can be used to attach biotin to one of the molecules (e.g., attach biotin to the binding agent). The nucleic acid sequence encoding streptavidin can then be ligated to the nucleic acid sequence encoding the other molecule (in this case the sortase A recognition sequence). The resulting protein can then be expressed using standard recombinant biology and cell culture techniques (see Ausubel et al., supra). The resulting biotinylated binding agent and streptavidin-sortase recognition sequence fusion protein are operably linked to one another via the streptavidin/biotin interaction. Similarly, the GST fusion protein system has been described (see U.S. Pat. No. 5,654,176) and is available commercially from multiple sources (e.g., from Merck, Pierce, Abnova, etc.).

Figure 4:
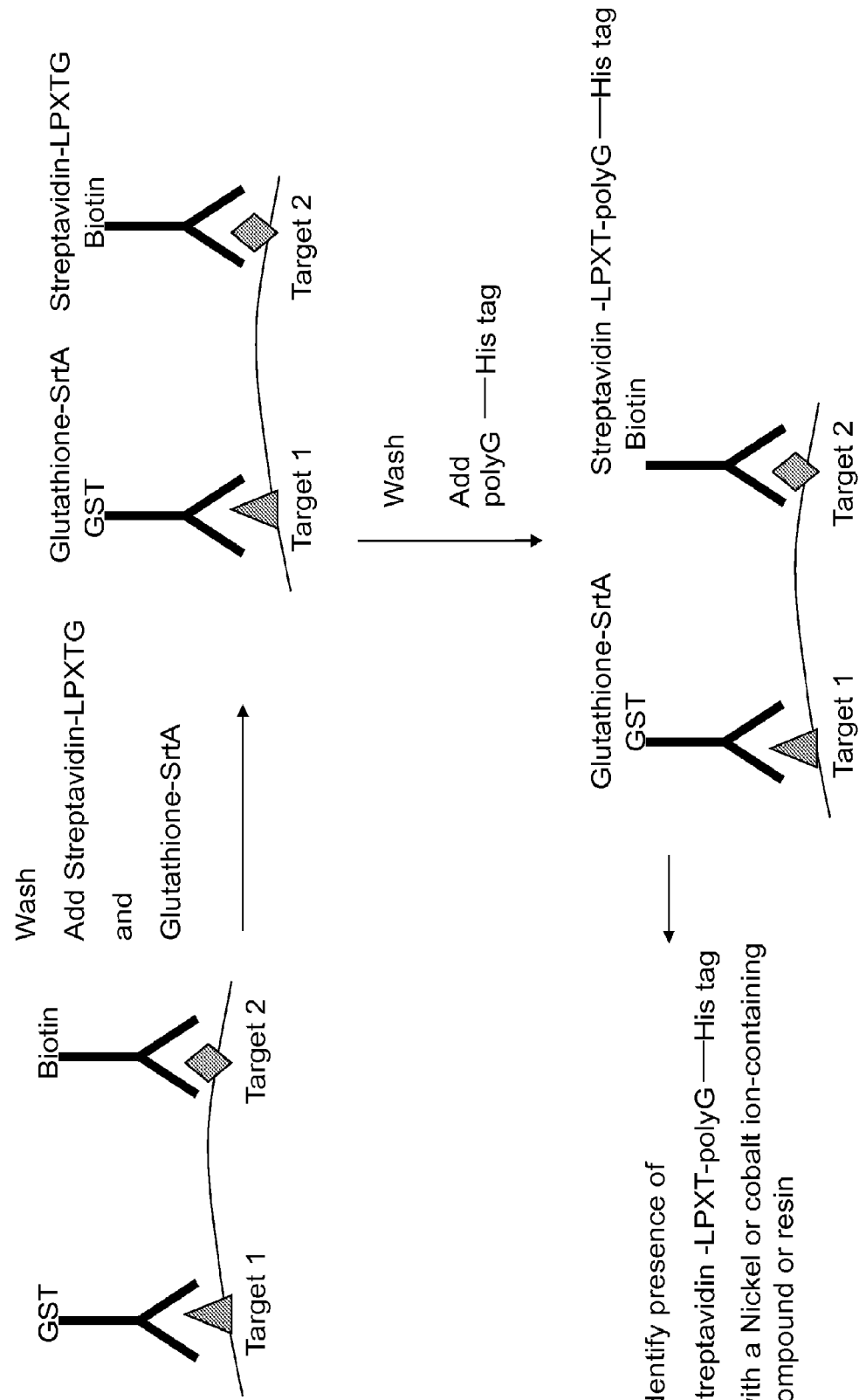
FIG. 4 is a schematic representation of a non-limiting embodiment of the present disclosure using binding member pair partners.

A non-limiting example of an embodiment of the present disclosure utilizing the GST/glutathione, the streptavidin/biotin, and the His-tag/metal divalent ion binding member pairs is depicted in FIG. 4. In FIG. 4, the binding agent that specifically binds to Target 1 is directly attached to glutathione S-transferase (GST) and the binding agent that specifically binds to Target 2 is directly attached to biotin (i.e., the binding agent is biotinylated). After washing to remove any unbound binding agent, a sortase A-glutathione fusion protein and a sortase A recognition sequence-streptavidin fusion protein are added. The two fusion proteins will specifically bind the binding agents via their binding members (i.e., the sortase A-glutathione fusion protein will specifically bind the GST-attached binding agent that specifically binds to Target 1 and the sortase A recognition sequence-streptavidin fusion protein will specifically bind to the biotinylated binding agent that specifically binds to Target 2. After washing to remove any unbound fusion proteins, a His tagged sortase substrate is added. If both Target 1 and Target 2 are present, sortase A will ligate the LPXT portion of the sortase recognition sequence operably linked to the biotinylated binding agent to the HA tagged sortase substrate. The ligation product can then be detected by passing the biological sample over a Ni-NTA resin (e.g., commercially available from Qiagen, Germantown, Md.) and determining if the ligation reaction took place (e.g., determining if streptavidin is present in the ligation product using, for example, an anti-biotin antibody.

In further aspect, the present disclosure provides kits for detecting multiple targets concurrently comprising a first sortase recognition sequence directly attached to a first member of a first binding member pair, a first sortase molecule directly attached to a first member of a second binding member pair; a sortase substrate; and instructions for using the kit to detect the concurrent presence of at least two targets. In some embodiments, the multiple targets are within a biological sample.

In some embodiments, the sortase substrate directly attached to a first member of a third binding member pair. In some embodiments, the kit further comprises a detectable second member of the third binding member pair.

Thus, a non-limiting kit may include a first member of a first binding member pair directly attached to a sortase molecule, a second member of a second binding member pair directly attached to a sortase recognition sequence, and a sortase substrate.

In some embodiments, the sortase substrate is directly attached to an antigen. In some embodiments, the kit further comprises an antibody (e.g., a detectable antibody) that specifically binds to the antigen. In some embodiments, the sortase substrate is directly attached to a first member of a third binding member pair. In some embodiments, the kit further comprises a second member of the third binding member pair. In some embodiments, the second member of the third binding member pair is detectable.

In some embodiments, the first binding member pair and the second binding member pair is each an antibody/antigen pair, where the antigen is an Fc portion of an antibody of a species and the antibody specifically binds to the Fc portion of the antibody of the species, wherein the species of the first binding member pair and the species of the second binding member pair are not the same. For example, one species could be a rabbit and the other species could be a rat, or one species could be a mouse and the other species could be a rabbit.

Accordingly, in some embodiments, a non-limiting kit comprises a first antibody that specifically binds to antibodies of a first species, said first antibody directly attached to a sortase molecule, a second antibody specifically binds to antibodies of a second species, said second antibody directly attached to a sortase recognition sequence, and a sortase substrate. In some embodiments, the sortase substrate is directly attached to an antigen. In some embodiments, the kit further comprises an antibody (e.g., a detectable antibody) that specifically binds to the antigen.

The first species may be, for example, a rabbit and the second species may be, for example, a mouse.

The methods and kits disclosed herein are useful for detecting co-expression of two targets in a biological sample. As used herein, the term "biological sample" refers to saliva, cells, mucous, tears, blood, serum, lymph/interstitial fluids, buccal cells, mucosal cells, cerebrospinal fluid, semen, feces, plasma, urine, marrow, a suspension of cells, or a suspension of cells and viruses or extracts or any of the foregoing, and may comprise a cell, chromosomes isolated from a cell (e.g., a spread of metaphase chromosomes), genomic DNA (in solution or bound to a solid support such as for Southern analysis), RNA (in solution or bound to a solid support such as for northern analysis), cDNA (in solution or bound to a solid support) obtainable from any mammal (e.g., a human), such as a normal mammal or a mammal having or suspected of having a condition such as cancer or heart disease. In some embodiments, a biological sample is mammalian (e.g., human) and is a biopsy sample or a blood sample including a circulating tumor cell. Biological samples useful in the practice of the methods of the disclosure may be obtained from any mammal.

Any biological sample comprising cells (or extracts of cells) from an animal is suitable for use in the methods of the disclosure. In one embodiment, the biological sample comprises cells obtained from a tissue biopsy. A tumor biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor, and techniques for obtaining such aspirates are well known in the art (see Cristallini et al., *Acta Cytol.* 36: 416-22 (1992)).

In some embodiments, the biological sample comprises circulating tumor cells. Circulating tumor cells ("CTCs") may be purified, for example, using the kits and reagents sold under the trademarks Vita-Assays™, Vita-Cap™, and CellSearch® (commercially available from Vitatex, LLC (a Johnson and Johnson corporation). Other methods for isolating CTCs are described (see, for example, PCT Publication No. WO2002/020825, Cristofanilli et al., New Engl. J. Med. 351:781-791 (2004), and Adams et al., J. Amer. Chem. Soc. 130: 8633-41 (July 2008)). In a particular embodiment, a circulating tumor cell ("CTC") may be isolated and identified as having originated from the kidney.

In various embodiments, the animal from which the biological sample originates) is a human, and the human may have or may be suspected of having a disease condition such as cancer or heart disease. In another embodiment, the mammal is large animal, such as a horse or cow, while in other embodiments, the mammal is a small animal, such as a dog or cat, all of which are known to develop disease conditions.

Any biological sample comprising cells (or extracts of cells) from an animal having or suspected of having a disease condition is suitable for use in the methods of the disclosure. In one embodiment, the biological sample comprises cells obtained from a tissue biopsy (e.g., from a cancer or suspected cancer). The biopsy may be obtained, according to standard clinical techniques, from primary tumors occurring in an organ of a mammal, or by secondary tumors that have metastasized in other tissues. In another embodiment, the biological sample comprises cells obtained from a fine needle aspirate taken from a tumor by methods well known in the art (see Cristallini et al., *Acta Cytol.* 36: 416-422 (1992)).

Cellular extracts of the foregoing biological samples may be prepared, either crude or partially (or entirely) purified, in accordance with standard techniques, and used in the various methods of the disclosure. Alternatively, biological samples comprising whole cells may be utilized in assay formats such as immunohistochemistry (IHC), flow cytometry (FC), and immunofluorescence (IF), as further described herein. Such whole-cell assays are advantageous in that they minimize manipulation of the tumor cell sample and thus reduce the risks of altering the in vivo signaling/activation state of the cells and/or introducing artifact signals. Whole cell assays are also advantageous because they characterize expression and signaling only in tumor cells, rather than a mixture of tumor and normal cells.

In some embodiments, the methods utilize a non-limiting member of the sortase family, namely Sortase A. In some embodiments, the Sortase A is from *Staphylococcus aureus*. Sortase A is able to ligate (i.e., join) two molecules, where each molecule comprises one of two moieties: 1) an LPXTG (SEQ ID NO: 1) motif, where LPXTG (SEQ ID NO: 1) are the single-letter codes for the amino acids Leucine (i.e., L), Proline (i.e., P), any amino acid residue (i.e., X), Threonine (i.e., T) and Glycine (i.e., G): and 2) a poly-glycine motif comprising at least three adjacent Glycine residues, or four adjacent Glycine residues, or five adjacent Glycine residues.

To perform the ligation, Sortase A (a non-limiting member of the sortase family of enzymes) cleaves between the Gly and Thr of the LPXTG (SEQ ID NO: 1) motif and catalyses the formation of an amide bond between the carboxyl-group of threonine and the amino-group of one of the glycine residues in the poly-glycine motif bearing peptide.

Thus in various non-limiting aspects, the present disclosure utilizes a first and a second modified antibody species, each recognizing a unique target within a biological sample. Attached to the first species is the enzyme, sortase A (SrtA) or a biologically active fragment thereof. By "biologically active" refers to a protein having structural, regulatory, or biochemical functions of a naturally occurring molecule. Thus, a biologically active fragment of a sortase enzyme is the meant a fragment of the full length sortase enzyme sufficient to perform the ligation between a motif bearing a "LPXT" sequence and a motif bearing a "GGG" sequence. Attached to the second antibody species is a motif comprising the LPXTG (SEQ ID NO: 1) recognition sequence for SrtA-mediated molecular ligation. Binding of the first and second antibody species to their respective targets within the biological sample, and the subsequent addition of a $(G)_{5x}$-ligand will result in the SrtA-mediated ligation of the ligand to the LPXTG (SEQ ID NO: 1) sequence attached to the first antibody species. Subsequent detection of the ligation product will indicate the concurrent presence of both targets within the biological sample.

In certain embodiments the ligation product can be detected using a third antibody that is conjugated to a detectable moiety for colorimetric detection (e.g., where the detectable moiety is horse radish peroxidase—HRP), chemiluminescent detection (e.g., where the detectable moiety is alkaline phosphatase—AP) or fluorescent detection (e.g., where the detectable moiety is fluorophore such as FITC or phycoerythrin). Such conjugation can be performed as described above. Detection can be performed using standard methods (e.g., an ELISA plate reader, FACS scanning, immunohistochemistry, etc. . . . ).

Thus, in various embodiments, the molecules used in the methods and kits of the disclosure are operably linked to a detectable moiety. By "detectable" with respect to a molecule (e.g., a target, a ligand, a polypeptide, a polynucleotide, or a binding agent (e.g., an antibody)) disclosed herein means a chemical, biological, or other modification of or to the molecule to operably link that molecule to a detectable moiety. Detectable moieties includes, without limitation, fluorescent labels, mass labels, residue labels (e.g., attachment of a antigen), dyes, radioisotopes, or tag (e.g., a HIS tag; see U.S. Pat. No. 4,569,794 or a GST tag; see U.S. Pat. No. 5,654,176), by which the presence of the modified molecule may be detected.

The methods of the disclosure can be performed using any immunological assay with the binding agents described herein.

Immunoassay formats and variations thereof, which may be useful for carrying out the methods disclosed herein, are well known in the art. See generally E. Maggio, Enzyme-Immunoassay, (1980) (CRC Press, Inc., Boca Raton, Fla.); see also, e.g., U.S. Pat. No. 4,727,022 (Skold et al., "Methods for Modulating Ligand-Receptor Interactions and their Application"); U.S. Pat. No. 4,659,678 (Forrest et al., "Immunoassay of Antigens"); U.S. Pat. No. 4,376,110 (David et al., "Immunometric Assays Using Monoclonal Antibodies"). Conditions suitable for the formation of reagent-antibody complexes are well known to those of skill in the art. See id. Binding agents may be used in a "two-site" or "sandwich" assay, with a single hybridoma cell line serving as a source for both the labeled monoclonal antibody and the bound monoclonal antibody. Such assays are described in U.S. Pat. No. 4,376,110. The concentration of detectable reagent that detects the ligation product should be sufficient such that the binding of the ligation product (if present) is detectable compared to background.

Antibodies useful in the practice of the methods disclosed herein may be conjugated to a solid support suitable for a diagnostic assay (e.g., beads, plates, slides or wells formed from materials such as latex or polystyrene) in accordance with known techniques, such as precipitation. Antibodies or other binding reagents binding reagents may likewise be conjugated to detectable groups such as radiolabels (e.g., $^{35}S$, $^{125}I$, $^{131}I$), enzyme labels (e.g., horseradish peroxidase, alkaline phosphatase), and fluorescent labels (e.g., fluorescein) in accordance with known techniques.

Cell-based assays, such flow cytometry (FC), immunohistochemistry (IHC), immunocytochemistry (ICC), or immunofluorescence (IF) are particularly desirable in practicing the methods of the disclosure, since such assay formats are clinically suitable, allow the detection of a sortase-mediated ligation product in vivo, and avoid the risk of artifact changes in activity resulting from manipulating cells obtained from, e.g. a tumor sample in order to obtain extracts. Accordingly, in some embodiments, the methods are implemented in a flow-cytometry (FC), immunocytochemistry (ICC), immuno-histochemistry (IHC), or immunofluorescence (IF) assay format.

Flow cytometry (FC) may also be employed to determine the presence of a sortase-mediated ligation product. Flow cytometry may be carried out according to standard methods. See, e.g. Chow et al., Cytometry (Communications in Clinical Cytometry) 46: 72-78 (2001). Briefly and by way of example, the following protocol for cytometric analysis may be employed: fixation of the cells with 2% paraformaldehyde for 10 minutes at 37° C. followed by permeabilization in 90% methanol for 10 minutes on ice. Cells may then be contacted with the primary antibodies (e.g., that specifically bind to target 1 and target 2), washed and the sortase substrate and detectable reagent that detects presence of the sortase-mediated ligation product added. The cells would then be analyzed on a flow cytometer (e.g. a Beckman Coulter FC500) according to the specific protocols of the instrument used. Such an analysis would identify the level of the sortase-mediated ligation product and thus identify whether both target 1 and target 2 were present. For disease conditions (e.g., cancer or heart disease) similar analysis after treatment of the patient with therapeutic would reveal the responsiveness of the patient to the targeted therapeutic.

Immunohistochemical (IHC) staining may be also employed to determine the concurrent presence of two or more targets in a biological sample taken, for example, from a patient with a disease condition (or suspected disease condition) such as cancer or heart disease before, during, and after treatment with a therapeutic intended to inhibit the disease condition. IHC may be carried out according to well-known techniques. See, e.g., ANTIBODIES: A LABORATORY MANUAL, Chapter 10, Harlow & Lane Eds., Cold Spring Harbor Laboratory (1988). Briefly, and by way of example, paraffin-embedded tissue (e.g. tumor tissue from a biopsy) is prepared for immunohistochemical staining by deparaffinizing tissue sections with xylene followed by ethanol; hydrating in water then PBS; unmasking antigen by heating slide in sodium citrate buffer; incubating sections in hydrogen peroxide; blocking in blocking solution; incubating the slide in primary antibodies (e.g., an ALK-specific antibody operably linked to Sortase A and an EGFR-specific antibody operably linked to a sortase A recognition sequence), washing, adding the sortase substrate, and finally detecting the sortase-mediated ligation product.

Immunofluorescence (IF) assays may be also employed to determine the concurrent presence of two or more targets in a biological sample of a patient with a disease condition (or suspected disease condition) taken before, during, and after treatment with a disease condition-targeting therapeutic. IF may be carried out according to well-known techniques. See, e.g., J. M. Polak and S. Van Noorden (1997) INTRODUCTION TO IMMUNOCYTOCHEMISTRY, 2nd Ed.; ROYAL MICROSCOPY SOCIETY MICROSCOPY HANDBOOK 37, BioScientific/Springer-Verlag. Briefly, and by way of example, patient samples may be fixed in paraformaldehyde followed by methanol, blocked with a blocking solution such as horse serum, incubated with modified primary antibodies (e.g., an ALK-specific antibody operably linked to Sortase A and an EGFR-specific antibody operably linked to a sortase A recognition sequence), washing, adding the sortase substrate, and finally detecting the sortase-mediated ligation product using, for example, a fluorescent dye (e.g., Alexa Fluor® 488) labeled antibody that specifically binds to the ligation product. Binding of the detectable antibody can be detected using, for example, an epifluorescent microscope.

A variety of other protocols, including enzyme-linked immunosorbent assay (ELISA), radio-immunoassay (RIA), and fluorescent-activated cell sorting (FACS), for detecting the concurrent presence of two targets in a biological sample are known in the art. Normal expression of the two targets (e.g., to determine if they normally are concurrently expressed) can be established by comparing the results of the methods of the disclosure (i.e., detection of a sortase-mediated ligation product) in biological samples taken from normal subjects (e.g., human) with the results in biological samples taken from subjects having or suspected of having a disease condition.

The amount of ligation product (i.e., indicating concurrent expression of the two targets) may be quantified by various methods, but preferably by photometric means. Quantities of the ligation product produced in the biological sample from the patient having or suspected of having a disease condition and biological samples normal patients are compared with the standard values. Deviation between standard and subject values establishes the parameters for diagnosing disease.

EXAMPLES

The following Examples are provided only to further illustrate the invention, and are not intended to limit its scope, except as provided in the claims appended hereto. The present invention encompasses modifications and variations of the methods taught herein which would be obvious to one of ordinary skill in the art. Materials, reagents and the like to which reference is made are obtainable from commercial sources, unless otherwise noted.

Example 1

In Vitro Sortase Reactions

Figure 5:
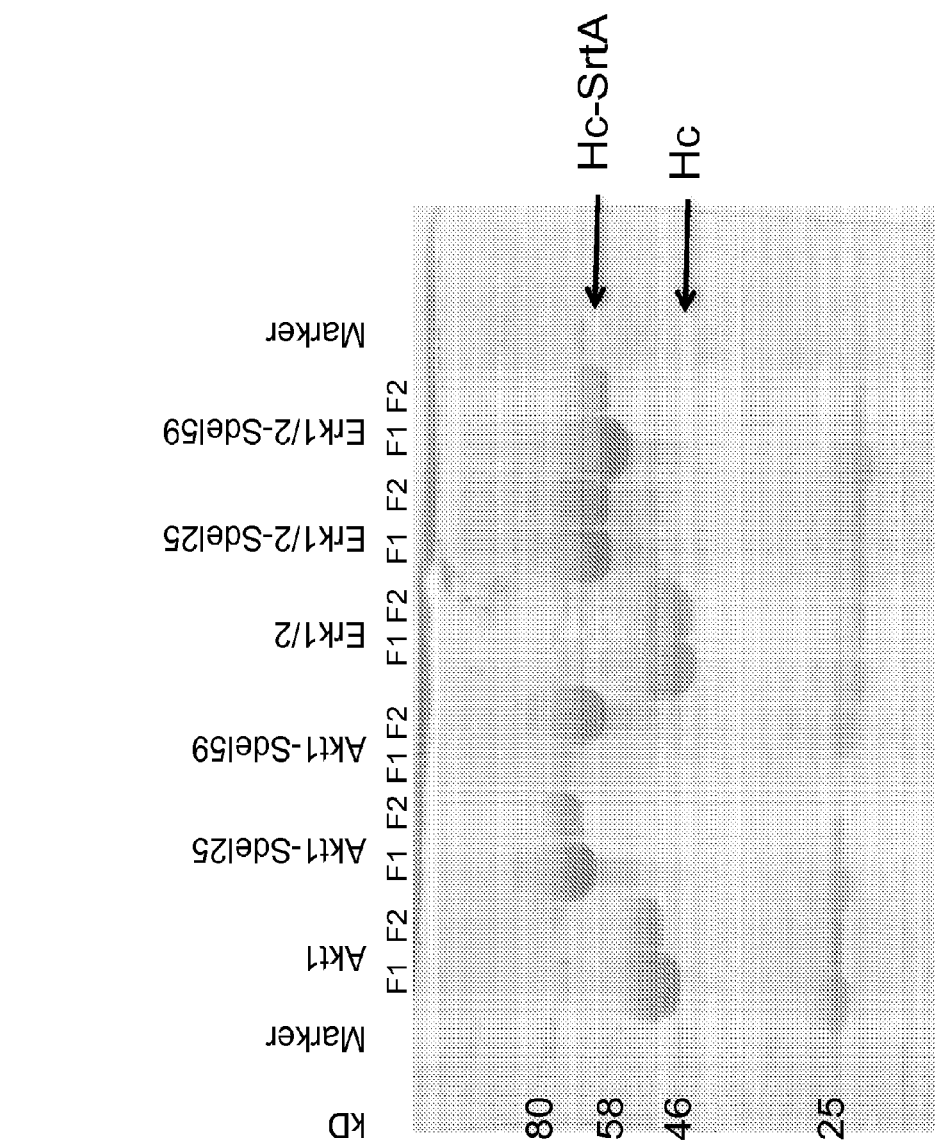
FIG. 5 is a photographic representation of electrophoretically resolved proteins on a 10% polyacrylamide gel stained with Coomassie blue showing the expression of rabbit IgG-SrtA fusion proteins. The proteins were electrophoretically resolved following recombinant expression of the fusion proteins and purification using protein A. Lanes F1 and F2: are elution fractions 1 and 2 from Protein A purification. Sdel25: first 25 amino acids of SrtA removed. Sdel59: first 59 amino acid of SrtA removed.

Rabbit antibody-SrtA fusion proteins were expressed as recombinant proteins by transfecting an expression vector encoding these proteins into a standard eukaryotic expression cell. Such cells are well known (e.g., COS cells, CHO cells, HeLa cells, SV40 cells, etc.). Expression constructs for antibody genes to Akt1 and Erk1/2, in which the heavy chain (Hc) gene is fused to genes encoding truncated forms of SrtA (Sdel25, Sdel59). A truncated form of Sortase A was used because the first 59 amino acid residues of *S. aureus* sortase A was found to be able to be removed without affecting the biological activity of Sortase A (see Ilangovan et al., *Proc. Nat'l. Acad. Sci.*, 98: 6056 (2001)). The sequence of SrtA (Sdel25) (which is missing the N-terminal 25 amino acids of wild-type *S. aureus* Sortase A) is provided in SEQ ID NO: 20 and the sequence of SrtA (Sdel59) (which is missing the N-terminal 59 amino acids of wild-type *S. aureus* Sortase A) is provided in SEQ ID NO: 21) These expression constructs encoding the fusion antibodies (i.e., encoding truncated sortase A-heavy chains and corresponding light chains) were similarly transfected into expression cell lines, and the recombinant Sortase A-tagged antibodies were isolated. The rabbit AB-SrtA fusion proteins were purified using Protein A (see FIG. 5).

```
SEQ ID NO: 20 (S. aureus SrtA del25):
KPHIDNYLHDKDKDEKIEQYDKNVKEQASKDNKQQAKPQIPKDKSKVAGY
IEIPDADIKEPVYPGPATPEQLNRGVSFAEENESLDDQNISIAGHTFIDR
PNYQFTNLKAAKKGSMVYFKVGNETRKYKMTSIRDVKPTDVEVLDEQKGK
DKQLTLITCDDYNEKTGVWEKRKIFVATEVK SEQ ID NO: 21 (S. aureus SrtA del59):
QAKPQIPKDKSKVAGYIEIPDADIKEPVYPGPATPEQLNRGVSFAEENES
LDDQNISIAGHTFIDRPNYQFTNLKAAKKGSMVYFKVGNETRKYKMTSIR
DVKPTDVEVLDEQKGKDKQLTLITCDDYNEKTGVWEKRKIFVATEVK
```

In certain embodiments, a spacer comprising amino acid sequence of variable lengths can be used between the binding agent (e.g., an antibody) and the sortase molecule or the sortase recognition sequence (i.e., the LPXTG motif (SEQ ID NO: 1) for Sortase A). The sortase-linked antibody may be designated AB-SrtA and the LPXTG-linked antibody may be designated AB-LPXTG. These SrtA and LPXTG (SEQ ID NO: 1) modified antibodies can be generated by gene fusion or bioorthogonal conjugation methodologies.

Figure 6:
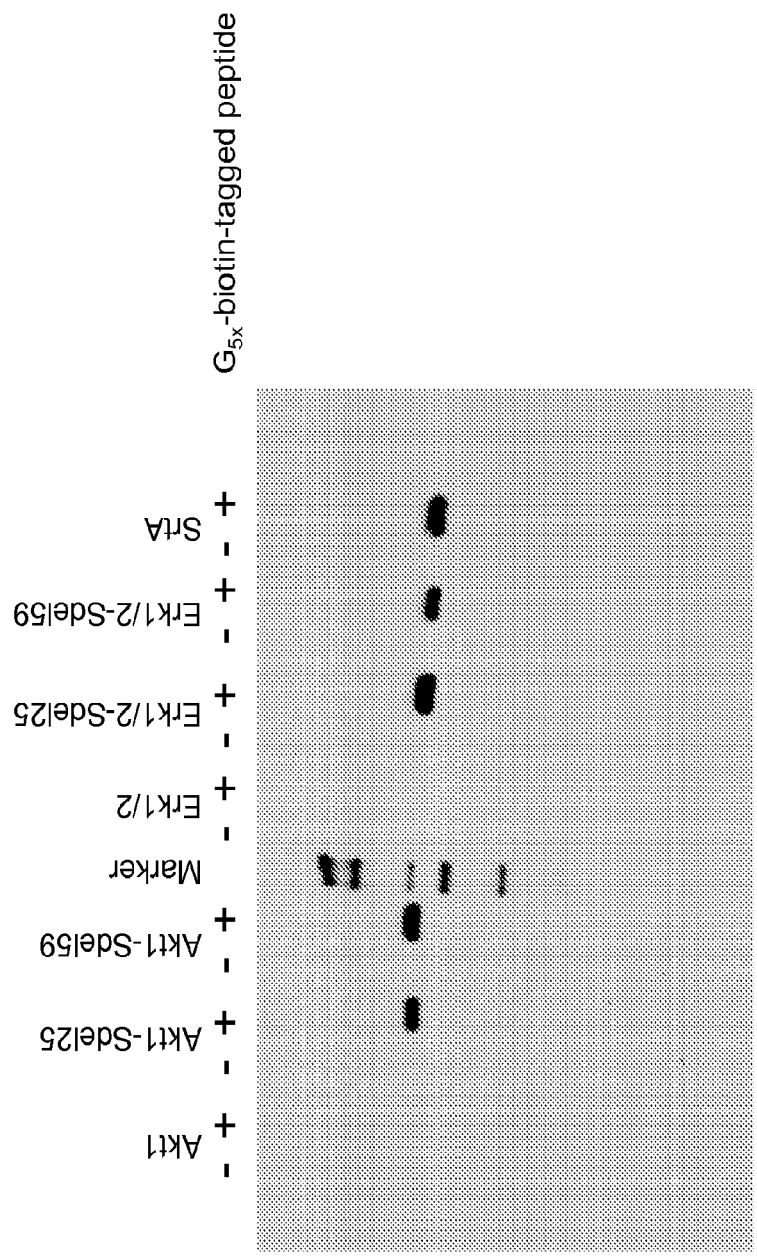
FIG. 6 is a photographic representation of western blotting analysis showing the sortase activity of the rabbit IgG-SrtA fusion proteins. Purified antibody (AB) alone or AB-SrtA fusions were tested as follows for sortase activity: Ligation reaction includes SrtA fusions, LPXTG (SEQ ID NO: 1) substrate (AB-LPXTG fusion), and with or without $G_{5x}$-biotin-tagged peptide ligand and $Ca^{2+}$ which stimulates sortase activity. Sortase activity results in the ligation of the $G_{5x}$-biotin-tagged peptide to the AB-LPXTG molecule, which is then visualized on a western blot using anti-biotin HRP (horse radish peroxidase). Wild-type sortase (SrtA), last pair of lanes, is included in the experiment as a positive control. Antibodies used are referred to by their respective targets. For example antibody to Akt1 is simply designated Akt1 unless specified otherwise.

Sortase activity of the AB-SrtA fusion was confirmed. As shown in FIG. 6, the sortase activity of the Akt1-SrtA (Sdel25), Akt1-SrtA(Sdel59), Erk1/2-SrtA(Sdel25), and Erk1/2-SrtA(Sdel59) fusions were compared to the activity of SrtA alone and each of the antibodies (i.e., lanes labeled Akt1 or Erk1/2) alone. All four of the AB-SrtA fusions showed comparable enzymatic activity to that of the SrtA alone. The activity of the antibodies alone (Akt1, Erk1/2) showed no enzymatic activity.

Binding specificity of the AB-SrtA fusions were confirmed. As shown in the tables set forth in FIGS. 7A-7C, the binding specificity of each of the Akt1-SrtA(Sdel59) and Erk1/2-SrtA(Sdel59) fusions were compared to the binding specificity of the antibodies alone. ELISA analysis was performed, showing that whereas the Erk1/2 antibody and the Erk1/2-SrtA(S59) fusion protein equivalently bind to an ELISA plate coated with the cognate Erk1/2 peptide (FIG. 7A), they fail to bind to both the Akt1 (FIG. 7B) and Stat3 (FIG. 7C) peptide coated plates. Corresponding results were observed with the Akt1 antibody and the Akt1-SrtA(Sdel59) fusion protein (i.e., the Akt1 antibody and the Akt1-SrtA (Sdel59) fusion protein bound to an ELISA plate coated with Akt1 (FIG. 7B) but failed to bind Erk1/2 peptide-coated plate (FIG. 7A) and Stat3-coated plate (FIG. 7C)). The Stat3 antibody was included as a negative "irrelevant antibody" control and predictably bound only the Stat3 peptide-coated plate (FIG. 7C).

To further demonstrate the various embodiments of the invention, an ELISA based assay was utilized. The experiment was conducted using ELISA plates that are coated with pair-wise combinations of the cognate peptides for the corresponding test SrtA and LPXTG-linked antibodies.

In this study, the antibodies were: Akt1 alone or fused with truncated forms of sortase, Sdel25 or Sdel59, along with ribosomal protein (rp) S6-LPXTG linked. The srtA and LPXTG (SEQ ID NO: 3) antibodies are first allowed to bind to an ELISA plate coated with either a combination of the cognate peptide for Akt1 and rpS6 or Akt1 and Stat3. After washing off unbound antibodies, reaction mixture with or without $G_{5x}$-biotin-tagged peptide ligand was incubated at 37° C. in neutral buffer (e.g., Phosphate-buffered saline (PBS) or Tris-buffered saline (TBS) at pH7.6 along with $Ca^{2+}$, which stimulates sortase activity. Detection of the ligated product is done using anti-biotin HRP secondary antibody. Samples were assayed in quadruplicates and the raw ELISA values of FIGS. 9A-9B were normalized in FIG. 8 with respect to test reactions without the $G_5$ biotin-tagged peptide ligand.

Figure 8:
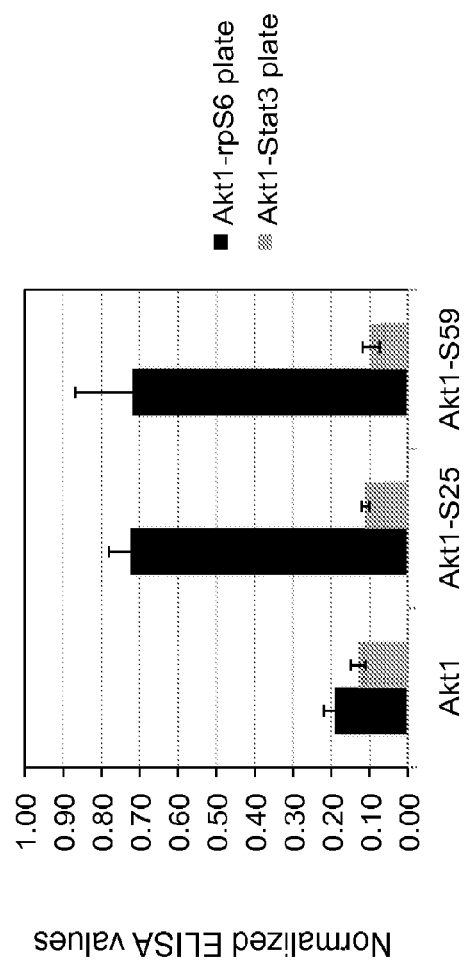
FIG. 8 is a bar graph depicting the results shown in FIGS. 9A-9B. Graphed are the average normalized values of the quadruplicate samplings, with the standard deviations depicted. Black bars depict the results on plates coated with Akt1 and rpS6 peptides; gray bars depict the results on plates coated with Akt1 and Stat3 peptides.

As shown in FIGS. 9A-9B, very low signal (or no signal) was observed in the absence of the substrate. FIG. 8 graphically depicts the results of FIGS. 9A-9B in which the rpS6-LPXTG linked antibody is tested with either Akt1 alone or fused to Sdel25 or Sdel59 sortase-A truncations. The results of FIG. 8 show that on the ELISA plate coated with Akt1-rpS6 peptide combination, a three to four fold increase in signal is observed with the SrtA-linked Akt1 antibody species compared to the native Akt1 antibody alone, indicating the signal is dependent on sortase activity (see also raw data in the tables of FIGS. 9A-9B). More importantly, this increase in signal is not observed on plates coated with Akt1-Stat3 peptide combination, indicating the requirement for engagement of both targets (See FIGS. 8 and 9B). These results validate the concept of the present invention.

Note that for all the experiments described above, sortase-mediated ligation was performed at 37° C. in a neutral buffered condition (e.g. Phosphate buffered saline (PBS) or Tris-buffered saline (TBS) at pH7.6.

Example 2

Simultaneous Detection of Intramolecular Targets

The methods described herein were next utilized where the two targets are present on the same molecule. In this example, the Sortase A (Sdel59) antibody specifically bound to MET kinase (regardless of phosphorylation status. A non-linked pMET antibody was used as a negative control. The second antibody was pMET-LPXTG linked antibody (i.e., this antibody specifically bound MET kinase only when MET kinase is phosphorylated). In the presence or absence of the G5x-biotin substrate, the sortase mediated reaction was allowed to occur as in Example 1 as assayed by ELISA on plates coated with pMET (i.e., phosphorylated MET) and MET peptides, plates coated with Akt1 and MET peptides, and plates coated with pMET and Akt1 peptides.

Figure 10:
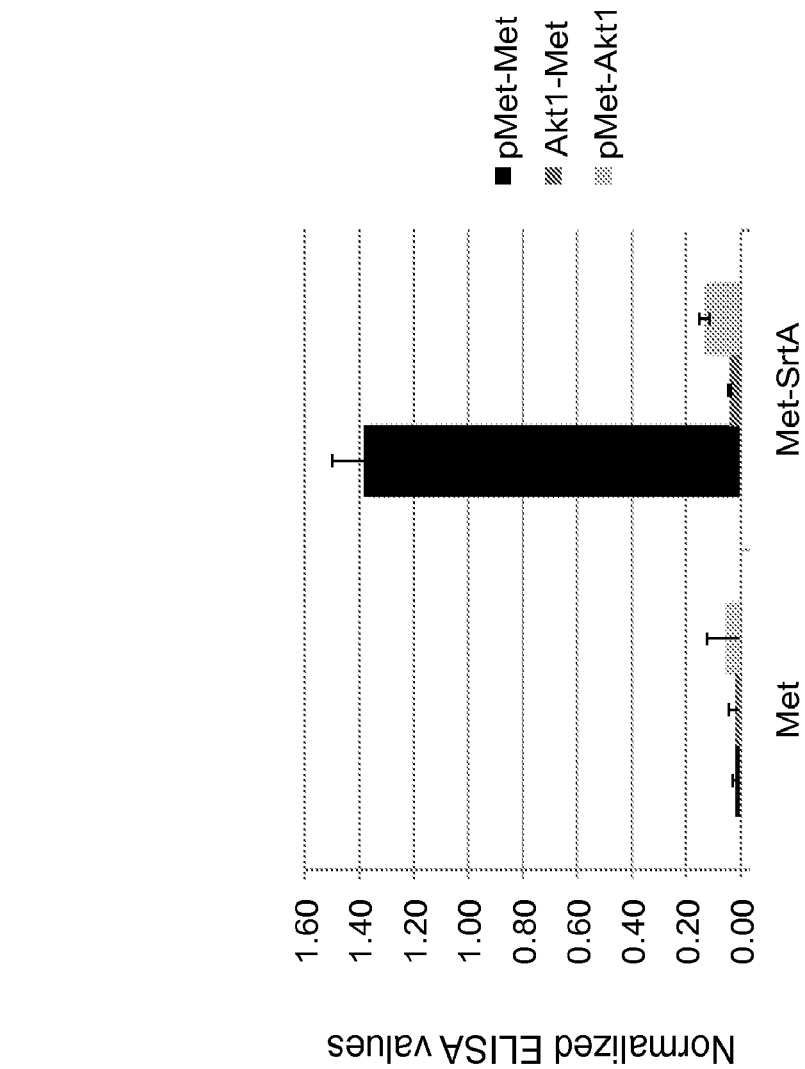
FIG. 10 is a bar graph depicting the results shown in FIGS. 11A-11C. Graphed are the average normalized values of the quadruplicate samplings, with the standard deviations depicted. Black bars depict the results on plates coated with pMET-MET (phosphorylated MET kinase and MET kinase respectively) peptides; gray bars depict the results on plates coated with Akt1-MET peptides; and light gray bars depict the results on plates coated with pMET-Akt1 peptides, and light gray bars depict the results on plates coated with Akt1 and phosphorylated MET kinase peptides

The results are shown in FIG. 11A-11C (raw data) and FIG. 10 (graphically depicting the data of FIGS. 11A-11C). FIG. 11A shows the results on plates coated with pMET and MET peptides. FIG. 11B shows the results on plates coated with Akt1 and MET peptides, and FIG. 11C shows the results on plates coated with pMET and Akt1 peptides. As predicted, the Sortase(Sdel59) MET-specific antibody and the MET-LPXTG linked antibody gave a signal only on the pMET-MET-coated plates (FIG. 11A and FIG. 10). No signal was found on the other plates, and no signal was observed by the non-sortase conjugated MET-specific antibody.

These results show that the methods of the various embodiments of the invention can potentially be used to identify the presence of two targets when those two targets are present on the same molecule (in this case, both targets might be present on a phosphorylated MET kinase molecule).

Example 3

Simultaneous Detection of Intramolecular Targets by Immunofluorescence

The methods described herein were next utilized in the immunofluorescence format. The antibody pair used was anti-EGFR linked to LPXTG (SEQ ID NO: 1) recognition motif (EGFR-LPXTG) and anti-phospho-EGFR linked to sortase (pEGFR-SrtA). Both antibodies were rabbit antibodies. Experiments were done on A431 carcinoma cells (commercially available from the American Type Culture Collection, Manassas, Va.), which overexpress EGFR, and upon stimulation with EGF (epidermal growth factor), the EGFR in these cells is phosphorylated. Standard immunofluorescence protocol was used: briefly, EGFR-LPXTG and pEGFR-SrtA were first allowed to bind to fixed A431 cells, that had been either treated with EGF or untreated; after washing to remove unbound antibodies, the G5x-HA peptide (i.e., GGGGG-linked hemagglutinin) was added along with $CaCl_2$ and incubated overnight to allow sortase ligation. Ligated products were detected by sequential staining with mouse anti-HA followed by anti-mouse-Alexa 488. Hoescht staining was also used to highlight the nuclei, as well as anti-rabbit-Alexa647 to detect the EGFR antibodies (and by proxy the localization of the EGFR).

Figure 12:
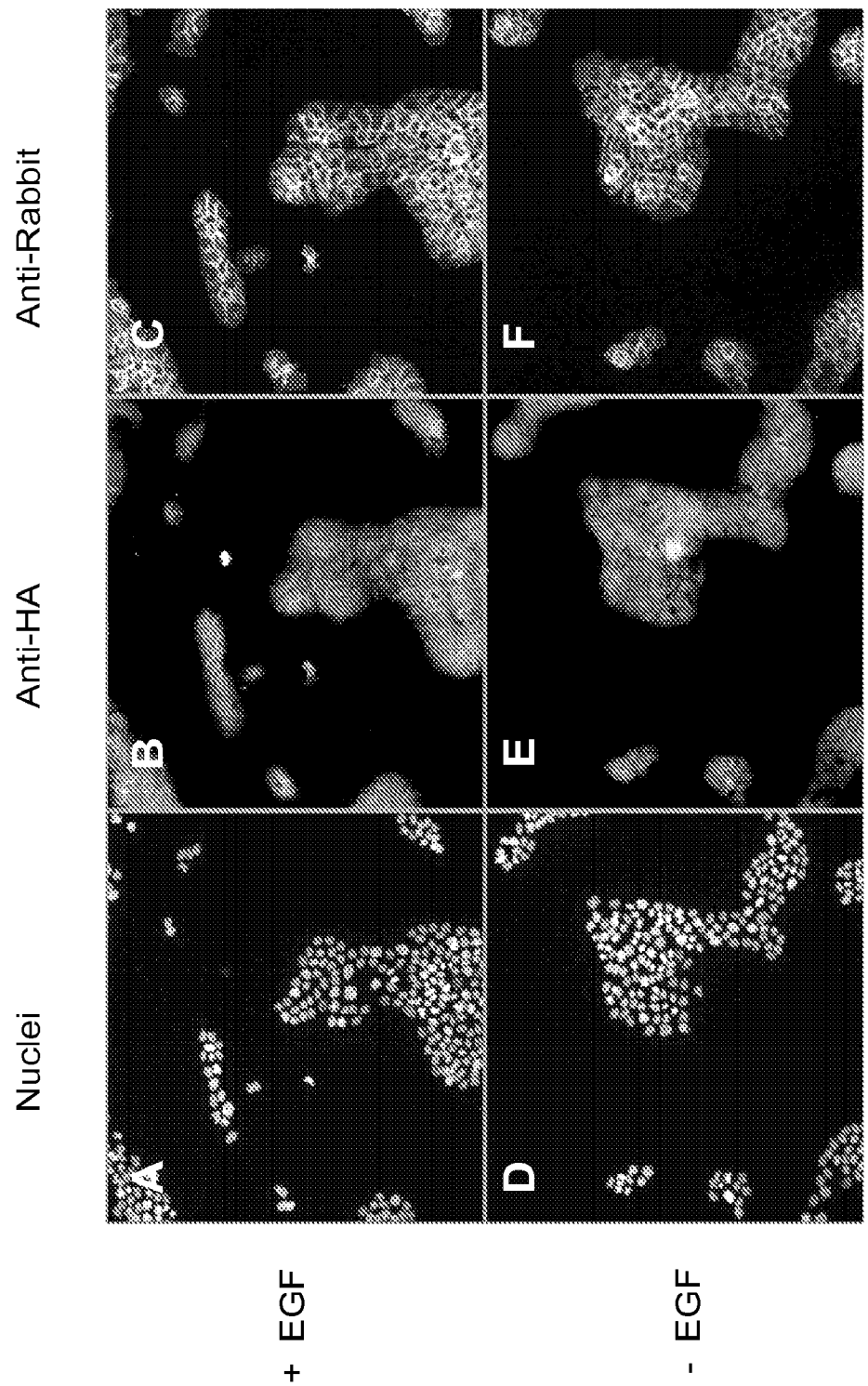
FIGS. 12A-12F are photographs showing the results of an immunofluorescence experiment.

As FIG. 12 shows specific membrane localized signals is observed only in the EGF treated cells (FIGS. 12B and 12C) and not in the untreated (FIGS. 12E and 12F), indicating that both targets (EGFR and phospho-EGFR) need to be present for sortase mediated ligation to occur. These results further indicate that the invention can be applied to the immunofluorescence format.

Figure 13:
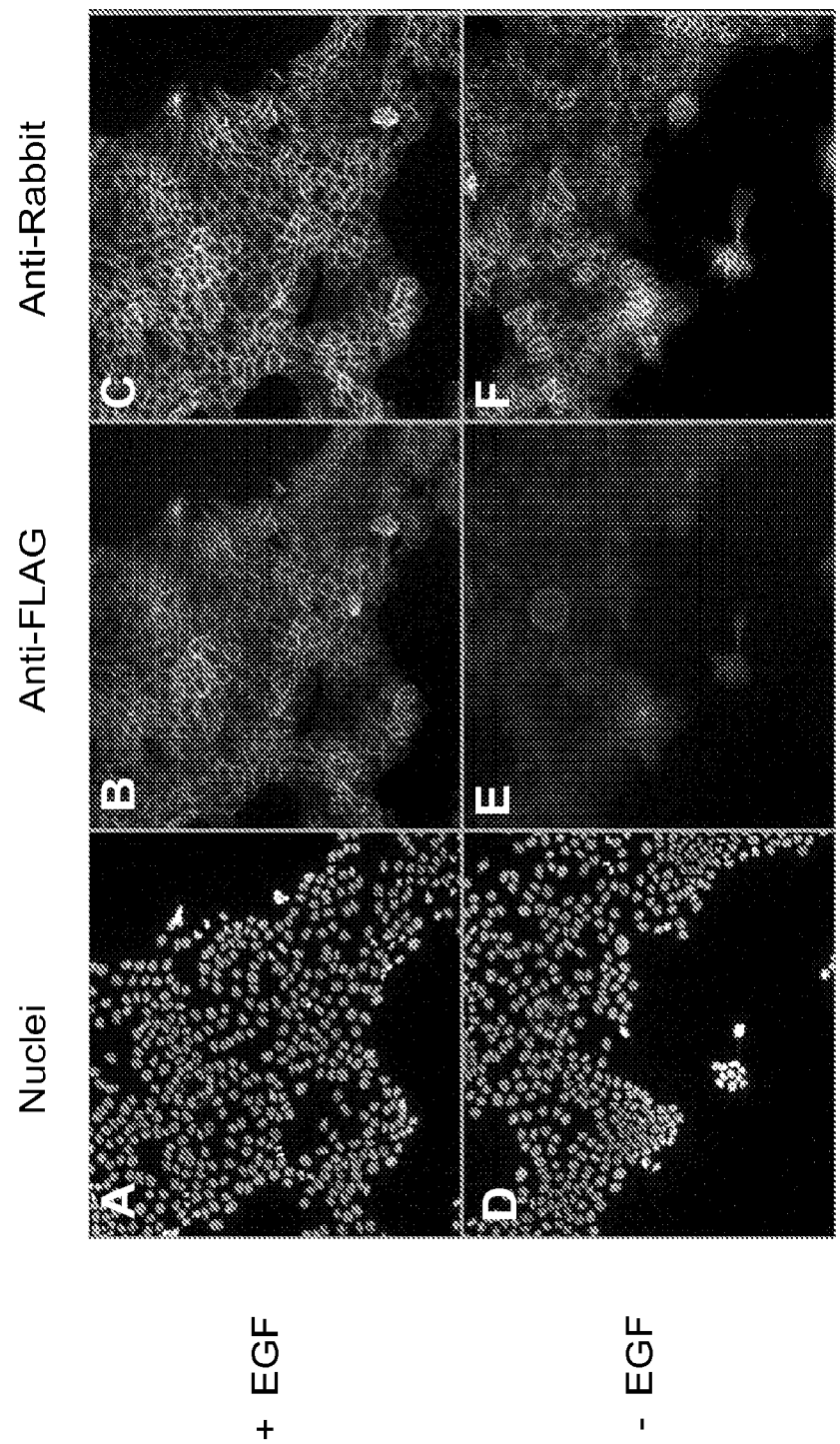
FIGS. 13A-13F are photographs showing the results of an immunofluorescence experiment.

The technology was also demonstrated using the peptide tag FLAG. As shown in FIG. 13 shows, when G5x-FLAG peptide was used in instead of the G5x-HA peptide, the signal to noise was greatly increased (e.g., compare FIGS. 13B and 13E). Experimental conditions and reagents including primary and secondary antibodies were as described above with the substitution of a mouse anti-FLAG antibody for the mouse anti-HA antibody.

Those skilled in the art will recognize, or be able to ascertain, using no more than routine experimentation, numerous equivalents to the specific embodiments described specifically herein. Such equivalents are intended to be encompassed in the scope of the following claims.

What is claimed is:

1. A method for detecting the concurrent presence of at least two targets within a biological sample, comprising:
   (a) contacting said biological sample with a first binding agent and a second binding agent, wherein said first binding agent is operably linked to a first sortase and specifically binds to a first target, and wherein said second binding agent is operably linked to a first sortase recognition sequence and specifically binds to a second target;
   (b) adding a sortase substrate under conditions where a first sortase-mediated ligation of the sortase substrate to the first sortase recognition sequence will produce a ligation product, and
   (c) detecting the ligation product, wherein detection of said ligation product indicates the concurrent presence of the first target and the second target in the biological sample.

2. The method of claim 1, wherein the first sortase is a Sortase A molecule.

3. The method of claim 2, wherein the Sortase A molecule is from *Staphylococcus aureus*.

4. The method of claim 1, wherein the first sortase recognition sequence comprises the amino acid sequence LPXTG, where X is any amino acid residue (SEQ ID NO: 1).

5. The method of claim 1, wherein the sortase substrate comprises the amino acid sequence GGG.

6. The method of claim 1, wherein detecting the ligation product is performed using a third binding agent that specifically binds to the ligation product.

7. The method of claim 1, wherein the first sortase is directly attached to the first binding agent.

8. The method of claim 1, wherein the first sortase is indirectly attached to the first binding agent.

9. The method of claim 1, wherein the first sortase recognition sequence is directly attached to the second binding agent.

10. The method of claim 1, wherein the first sortase recognition sequence is indirectly attached to the second binding agent.

11. The method of claim 1, wherein the first target and the second target are on the same molecule.

12. The method of claim 1, wherein the first binding agent is an antibody.

13. The method of claim 1, wherein the second binding agent is an antibody.

14. The method of claim 6, wherein the third binding agent is an antibody.

15. The method of claim 1, wherein the biological sample is selected from the group consisting of a cell, a biopsy sample, a blood sample, a tissue sample, a saliva sample, a tear sample, a semen sample, cerebrospinal fluid sample, a bone marrow sample, a bone marrow sample, and a circulating tumor cell sample.

16. The method of claim 1, wherein the biological sample is from a human.

17. A kit comprising a first sortase recognition sequence directly attached to a first member of a first binding member pair, a first sortase directly attached to a first member of a second binding member pair; a sortase substrate; and instructions for using the kit to detect the concurrent presence of at least two targets within a biological sample.

18. The kit of claim 17, wherein the sortase substrate is directly attached to a first member of a third binding member pair.

19. The kit of claim 18, further comprising a detectable second member of the third binding member pair.

20. A composition comprising an antibody operably linked to a sortase.

21. The method of claim 1, further comprising, prior to adding the sortase substrate, removing the first binding agent that is not bound to the first target and removing the second binding agent that is not bound to the second target.

* * * * *